(12) United States Patent
Uber, III et al.

(10) Patent No.: US 12,011,568 B2
(45) Date of Patent: Jun. 18, 2024

(54) FLUID DELIVERY SYSTEM INCLUDING A HIGH CRACK PRESSURE VALVE AND METHODS FOR ITS USE

(71) Applicant: BAYER HEALTHCARE LLC, Whippany, NJ (US)

(72) Inventors: Arthur Uber, III, Pittsburgh, PA (US); Mark Trocki, Cheswick, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 50 days.

(21) Appl. No.: 17/372,673

(22) Filed: Jul. 12, 2021

(65) Prior Publication Data

US 2021/0338922 A1 Nov. 4, 2021

Related U.S. Application Data

(63) Continuation of application No. 14/776,060, filed as application No. PCT/US2014/029152 on Mar. 14, (Continued)

(51) Int. Cl.
*A61M 5/172* (2006.01)
*A61M 5/00* (2006.01)
(Continued)

(52) U.S. Cl.
CPC ............ *A61M 5/172* (2013.01); *A61M 5/007* (2013.01); *A61M 5/16881* (2013.01); (Continued)

(58) Field of Classification Search
CPC ........ A61M 5/16881; A61M 2039/242; A61M 39/28
See application file for complete search history.

(56) References Cited

U.S. PATENT DOCUMENTS

| 4,096,879 A | 6/1978 | Serur et al. |
| 4,331,140 A | 5/1982 | Hallsey |

(Continued)

FOREIGN PATENT DOCUMENTS

| CN | 102003424 A | 4/2011 |
| CN | 102548606 A | 7/2012 |

(Continued)

OTHER PUBLICATIONS

The International Preliminary Report on Patentability and Written Opinion dated Sep. 24, 2015 from corresponding PCT Application No. PCT/US2014/029152.

(Continued)

*Primary Examiner* — Courtney B Fredrickson
(74) *Attorney, Agent, or Firm* — David Schramm; Joseph L. Kent; James R. Stevenson

(57) ABSTRACT

A high crack pressure valve is described. The high crack pressure valve includes an inlet adapted to receive a medical fluid pressurized by a pump; an outlet in fluid communication with a fluid path element, wherein the fluid path element is in fluid communication with downstream system components of a fluid delivery system; and a moveable element having a crack pressure threshold. The moveable element has a first closed position and a second open position and is configured to move from the first closed position to the second open position when a fluid pressure at the inlet is greater than or equal to the crack pressure threshold. The pressure of fluid at the outlet of the high crack pressure valve has little or no effect on movement of the moveable element from the first closed position to the second open position. Fluid injector systems and fluid path elements which include the high crack pressure valve are also described.

14 Claims, 15 Drawing Sheets

Related U.S. Application Data 2014, now Pat. No. 11,058,811, which is a continuation-in-part of application No. 13/831,667, filed on Mar. 15, 2013, now abandoned.

(51) Int. Cl.
| | | |
|---|---|---|
| *A61M 5/168* | (2006.01) | |
| *A61N 5/10* | (2006.01) | |
| *A61M 5/14* | (2006.01) | |
| *A61M 5/142* | (2006.01) | |
| *A61M 5/145* | (2006.01) | |
| *A61M 39/24* | (2006.01) | |

(52) U.S. Cl.
CPC ... *A61N 5/1002* (2013.01); *A61M 2005/1406* (2013.01); *A61M 5/14212* (2013.01); *A61M 5/1452* (2013.01); *A61M 5/16827* (2013.01); *A61M 2039/242* (2013.01); *Y10T 29/49826* (2015.01)

(56) References Cited

U.S. PATENT DOCUMENTS

| | | | |
|---|---|---|---|
| 4,369,780 A * | 1/1983 | Sakai | A61M 39/281 200/81.9 R |
| 4,631,055 A | 12/1986 | Redl et al. | |
| 4,759,527 A | 7/1988 | Brown | |
| 4,828,551 A | 5/1989 | Gertler et al. | |
| 5,490,499 A | 2/1996 | Heinonen et al. | |
| 5,739,508 A | 4/1998 | Uber, III | |
| 6,365,080 B1 | 4/2002 | Parise | |
| 6,595,950 B1 | 7/2003 | Miles et al. | |
| 7,306,736 B2 | 12/2007 | Collins et al. | |
| 7,308,300 B2 | 12/2007 | Toews et al. | |
| 7,462,166 B2 | 12/2008 | Kowan et al. | |
| 7,475,701 B2 | 1/2009 | Trocki et al. | |
| 8,096,316 B2 | 1/2012 | Trocki et al. | |
| 8,261,777 B2 | 9/2012 | Doig | |
| 8,551,037 B2 | 10/2013 | Suchecki et al. | |
| 9,265,885 B2 | 2/2016 | Strobl | |
| 9,498,570 B2 | 11/2016 | Cowan et al. | |
| 9,526,829 B2 | 12/2016 | Spohn et al. | |
| 9,555,379 B2 | 1/2017 | Schriver et al. | |
| 9,895,527 B2 | 2/2018 | Spohn et al. | |
| 9,901,671 B2 | 2/2018 | Toews et al. | |
| 9,913,941 B2 | 3/2018 | Miller et al. | |
| 2004/0055652 A1 | 3/2004 | Erickson | |
| 2004/0060999 A1 | 4/2004 | Kock | |
| 2006/0009739 A1 | 1/2006 | Poutiatine et al. | |
| 2006/0047368 A1 | 3/2006 | Maharajh et al. | |
| 2007/0083152 A1 | 4/2007 | Williams, Jr. et al. | |
| 2007/0129705 A1 | 6/2007 | Trombley et al. | |
| 2007/0219480 A1 | 9/2007 | Kamen et al. | |
| 2007/0219597 A1 | 9/2007 | Kamen et al. | |
| 2007/0272311 A1 | 11/2007 | Trocki et al. | |
| 2008/0041452 A1 | 2/2008 | Zweber | |
| 2008/0077081 A1 | 3/2008 | Mounce et al. | |
| 2008/0172006 A1 | 7/2008 | Hicks | |
| 2008/0195082 A1 | 8/2008 | Pauser et al. | |
| 2008/0281278 A1 | 11/2008 | Williams, Jr. et al. | |
| 2009/0149743 A1 | 6/2009 | Barron et al. | |
| 2009/0177180 A1 | 7/2009 | Rubalcaba, Jr. et al. | |
| 2009/0187083 A1 | 7/2009 | Blatcher et al. | |
| 2010/0147403 A1 | 6/2010 | Bresnahan | |
| 2010/0217232 A1 | 8/2010 | Rosenblatt | |
| 2010/0274179 A1 * | 10/2010 | Derichs | A61M 39/227 604/506 |
| 2011/0021905 A1 | 1/2011 | Patrick et al. | |
| 2011/0061752 A1 | 3/2011 | Hu | |
| 2011/0218495 A1 | 9/2011 | Remde | |
| 2012/0220949 A1 | 8/2012 | Davies et al. | |
| 2013/0049976 A1 | 2/2013 | Maggiore | |
| 2013/0075222 A1 | 3/2013 | Ari | |
| 2013/0123619 A1 * | 5/2013 | Griggs | G01L 7/00 600/432 |
| 2014/0188050 A1 | 7/2014 | Dittrich | |
| 2014/0261809 A1 | 9/2014 | Rife | |
| 2015/0011975 A1 | 1/2015 | Anderson et al. | |
| 2015/0202361 A1 | 7/2015 | Burns et al. | |
| 2016/0243346 A1 | 8/2016 | Vasko | |
| 2017/0100577 A1 | 4/2017 | Spohn et al. | |

FOREIGN PATENT DOCUMENTS

| | | |
|---|---|---|
| EP | 0323321 A1 | 7/1989 |
| JP | S63151149 U | 10/1988 |
| JP | H11299889 A | 11/1999 |
| WO | 8103689 A1 | 12/1981 |
| WO | 9800186 A1 | 1/1998 |
| WO | 0200291 A1 | 1/2002 |
| WO | 2006089157 A2 | 8/2006 |
| WO | 2006108775 A2 | 10/2006 |
| WO | 2007002613 A2 | 1/2007 |
| WO | 2007092618 A2 | 8/2007 |
| WO | 2009003500 A1 | 1/2009 |
| WO | 2012061140 A1 | 5/2012 |
| WO | 2013126318 A1 | 8/2013 |
| WO | 2015126526 A1 | 8/2015 |
| WO | 2015134717 A2 | 9/2015 |
| WO | 2015164783 A1 | 10/2015 |
| WO | 2016069711 A1 | 5/2016 |
| WO | 2016069714 A1 | 5/2016 |
| WO | 2016172467 A1 | 10/2016 |
| WO | 2018053074 A1 | 3/2018 |

OTHER PUBLICATIONS

Harvard Apparatus, Harvard Peristaltic Pump, Dec. 2012, www.harvardapparatus.com, Holliston, MA.

"International Preliminary Report on Patentability from PCT Application No. PCT/US2017/056757", dated May 2, 2019.

* cited by examiner

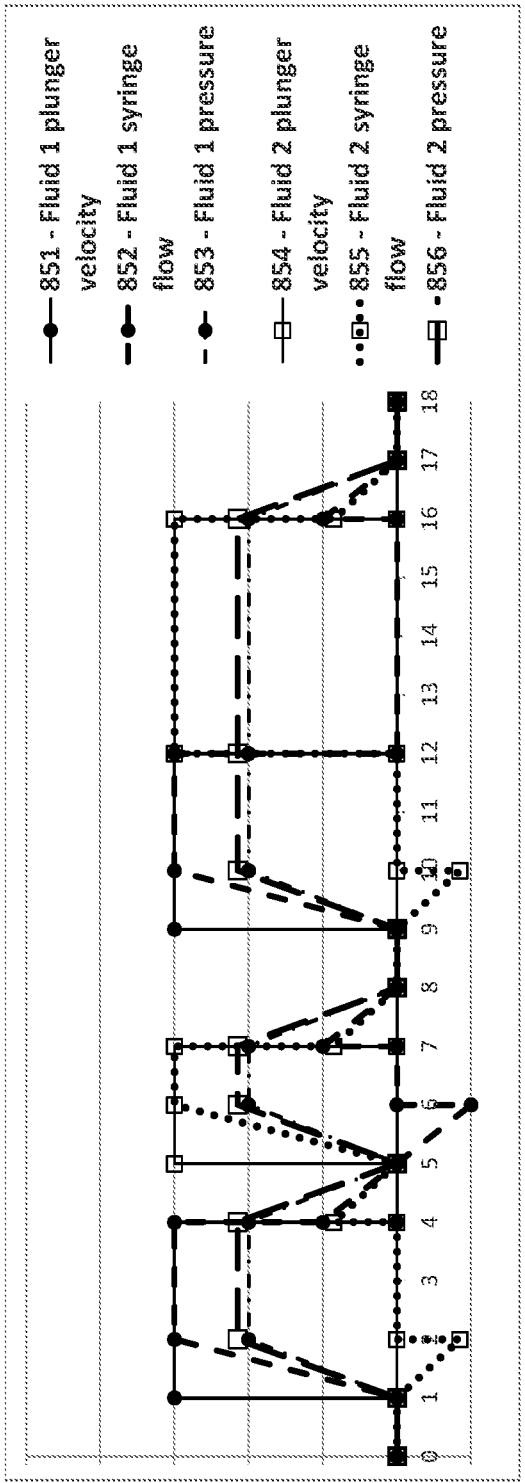
FIG. 9A
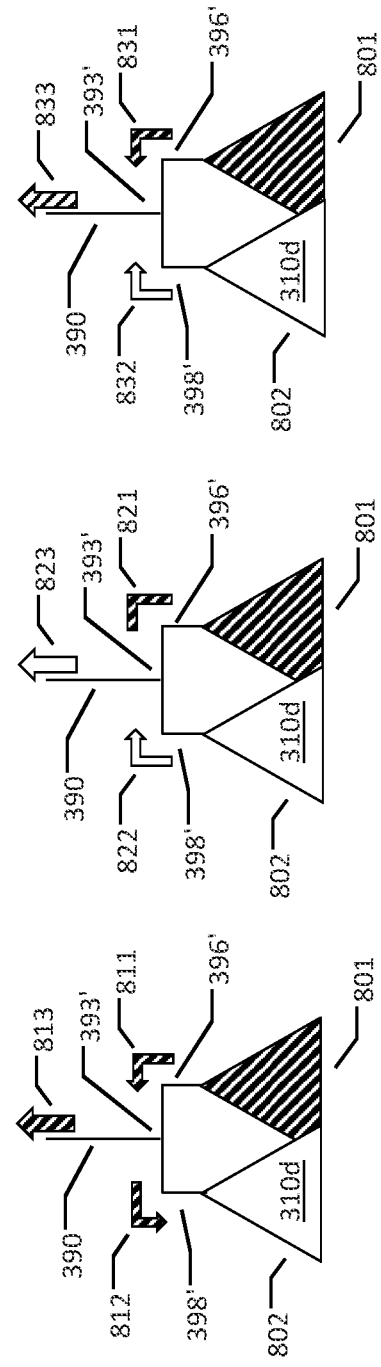
FIG. 9B
FIG. 9C
FIG. 9D

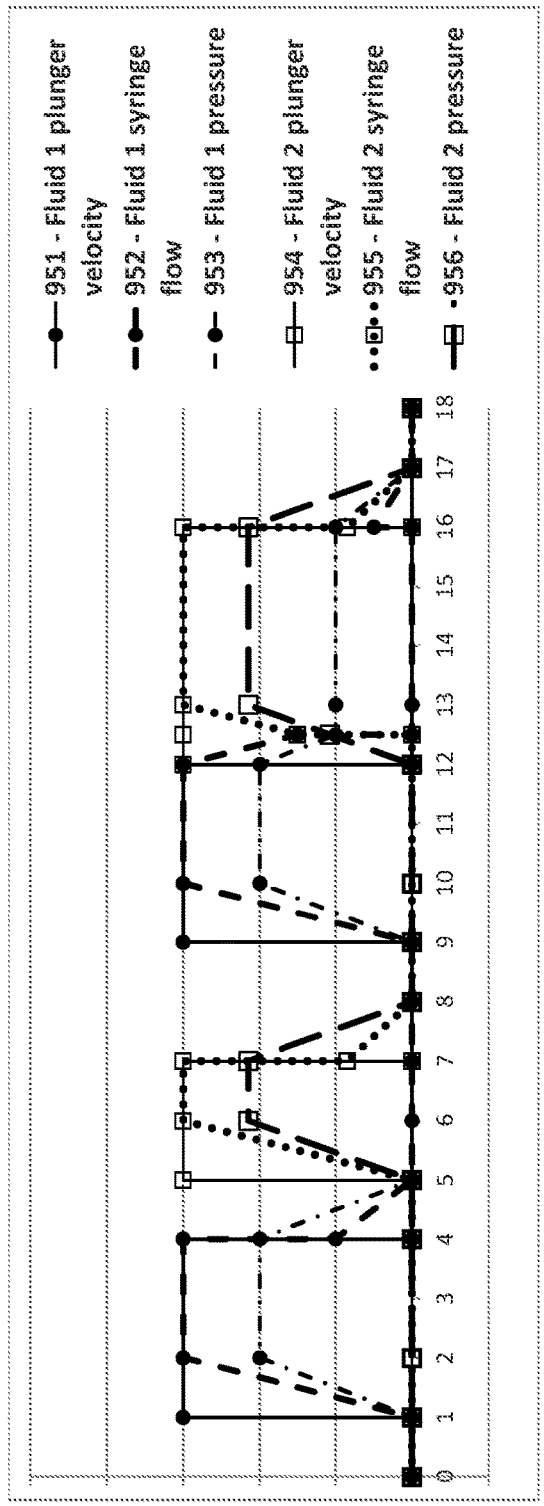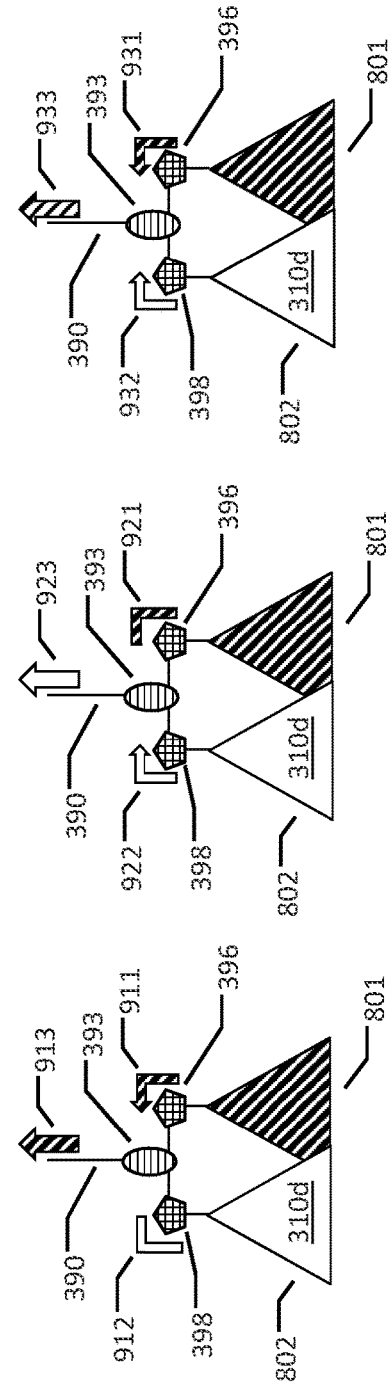
FIG. 10A
FIG. 10B
FIG. 10C
FIG. 10D

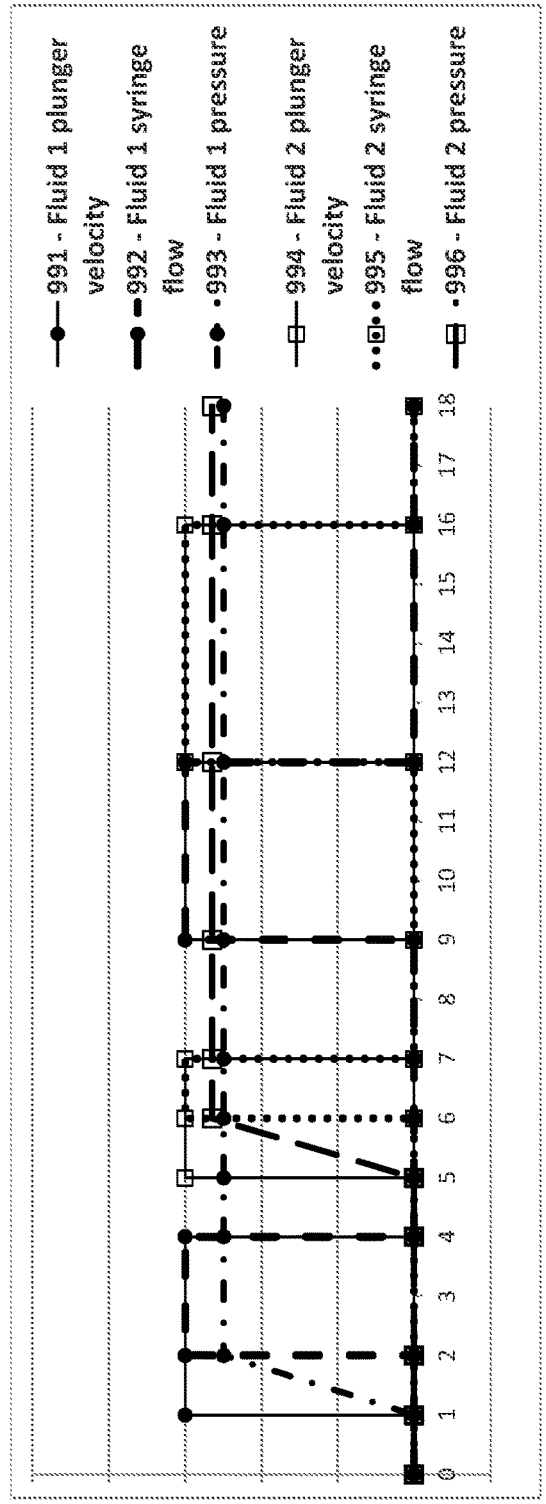
FIG. 11A
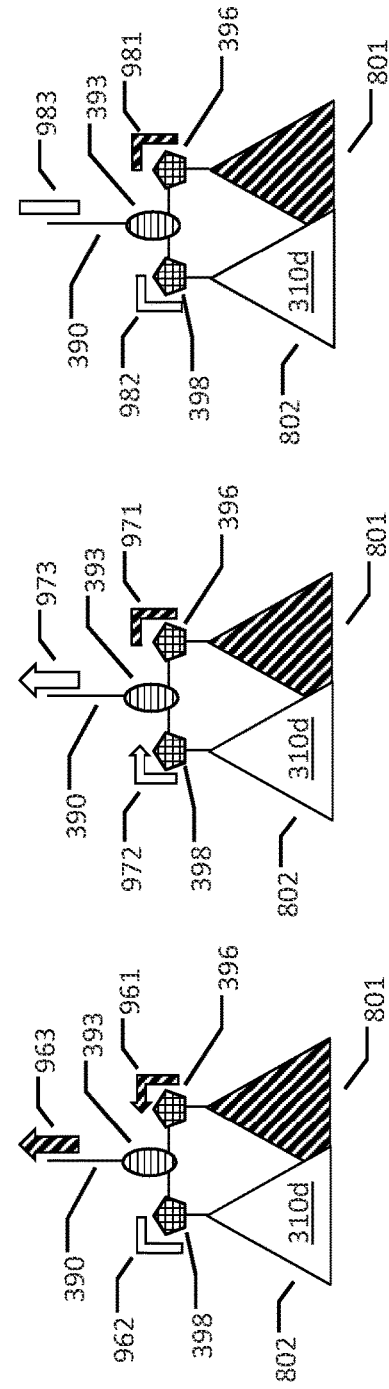
FIG. 11B
FIG. 11C
FIG. 11D

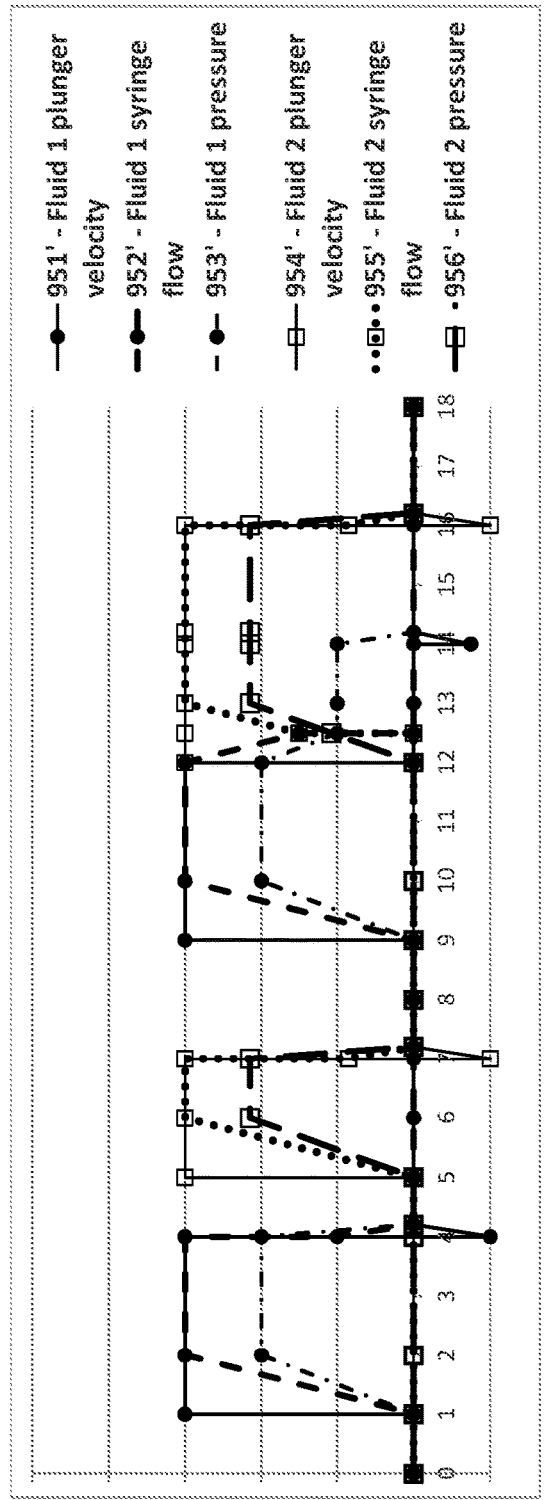
FIG. 12A
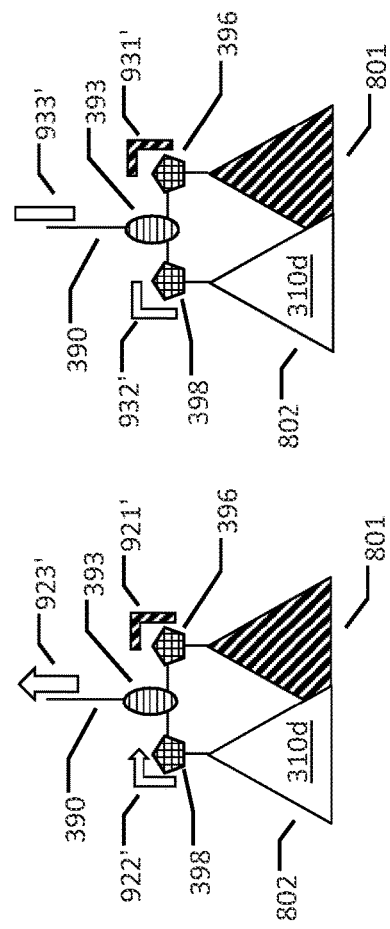
FIG. 12B
FIG. 12C
FIG. 12D

FLUID DELIVERY SYSTEM INCLUDING A HIGH CRACK PRESSURE VALVE AND METHODS FOR ITS USE

CROSS-REFERENCE TO RELATED APPLICATIONS

This application is a continuation of U.S. Ser. No. 14/776,060, having a 371(c) date of 14 Sep. 2015, which is a U.S. National Phase entry under 35 U.S.C. § 371 of International Application No. PCT/US2014/029152 filed 14 Mar. 2014, which continuation-in-part, and claims the benefit of U.S. patent application Ser. No. 13/831,667, filed 15 Mar. 2013, the disclosures of which are hereby incorporated by reference in their entirety.

BACKGROUND

Automated fluid delivery systems find many applications in medicine, veterinary practice, and animal research. The number of possible procedures, fluids, recipients, and conditions for fluid delivery may vary markedly. Procedures may include fluid delivery of antibiotics, saline, radiological contrast fluid, radioactive tracers, bone cement, gels, and gene therapy. The fluids may also include small molecules, macromolecules, gels, particles, cells, and viruses in any number of combinations. Recipients may include small rodents such as mice and rats, medium sized animals such as pigs and dogs, and humans. Volumes of injectate may range from about 1000 ml or more to less than about 1 µl, and delivery times may range from over about 1000 seconds (about 20 minutes) or more to less than 1 msec.

It is apparent that the variety of uses for fluid delivery systems suggests a variety of different systems, each optimized for the procedure, recipient, fluid, and/or condition for its intended use. It may be appreciated, both from the user's perspective as well as from the manufacturer's perspective, that the large number of possible fluid delivery systems may prove inconvenient. As one example, a small hospital may not be able to afford separate fluid delivery devices for antibiotic administration and the delivery of radiological contrast solutions for CT imaging. As another example, a medical researcher using animal models for human diseases may not wish to devote needed laboratory space to the number of injectors necessary to cover the wide variety of test animals including mice, dogs, and pigs. From the perspective of a manufacturer, it may be inefficient to develop one fluid delivery system to inject genetic material into a dog liver and then develop from scratch a second system to deliver radiological contrast material to a patient, since both systems are merely specific examples of a general system for introducing a fluid into a recipient.

It may, therefore, be appreciated that an intelligent and configurable fluid delivery system may reduce excess cost, space, and development time for both users and manufacturers, and provide flexibility to researchers to allow the development of new procedures that are not presently available with current equipment.

SUMMARY

In an embodiment, a configurable fluid delivery system may include a fluid delivery unit having at least one delivery unit data source, a fluid actuator unit in reversible mechanical communication with the fluid delivery unit, in which the fluid actuator unit has an actuator unit data source, and a control unit. The control unit may include a computing device having a non-transitory, computer-readable storage medium in operable communication with the computing device, the computing device further being in reversible or two way data communication with the fluid delivery unit and the fluid actuator unit, and an output device in operable communication with the computing device. Additionally, the computer-readable storage medium may contain one or more programming instructions that, when executed, may cause the computing device to receive delivery unit data from the delivery unit data source and actuator unit data from the actuator unit data source, determine a mechanical compatibility status between the fluid delivery unit and the fluid actuator unit based, at least in part, on the delivery unit data and the actuator unit data, transmit, to the output device, an output related to the mechanical compatibility status, determine a communication integrity status between two or more of the fluid delivery unit, the fluid actuator unit, and the control unit, transmit, to the output device, an output related to the communication integrity status, and transmit, to the output device, an output configuration for the fluid delivery system in a user understandable form, wherein the output configuration is dependent, at least in part, on one or more of the delivery unit data and the actuator unit data.

In an embodiment, a method of assembling a configurable fluid delivery device includes selecting a fluid delivery unit from one or more fluid delivery units, selecting a fluid actuator unit from one or more fluid actuator units, placing the fluid actuator unit in reversible mechanical communication with the fluid delivery unit, placing a control unit in reversible data communication with one or more of the fluid delivery unit and the actuator unit, transmitting, by the control unit to an output device, mechanical status data related to the reversible mechanical communication between the fluid actuator unit and the fluid delivery unit, and transmitting, by the control unit to an output device, communication status data related to the reversible data communication between one or more of the fluid delivery unit and the control unit, and the fluid actuator unit and the control unit.

In an embodiment, a fluid delivery device or system may incorporate a high crack pressure valve between a fluid pressurizing device and one or more fluid path elements conducting fluid to the patient or fluid recipient.

BRIEF DESCRIPTION OF THE DRAWINGS

FIGS. 9A-9D illustrate operation of the fluid delivery unit of FIG. 3D and an associated disposable unit with an exemplary fluid path element arrangement.

FIGS. 10A-10D illustrate operation of the fluid delivery unit of FIG. 3D and an associated disposable unit with another exemplary valving arrangement.

FIGS. 11A-11D illustrate operation of the fluid delivery unit of FIG. 3D and an associated disposable unit with yet another exemplary valving arrangement.

FIGS. 12A-12D illustrate operation of the fluid delivery unit of FIG. 3D and an associated disposable unit with a variation of the valving arrangement of FIGS. 10A-10D.

DETAILED DESCRIPTION

Figure 1:
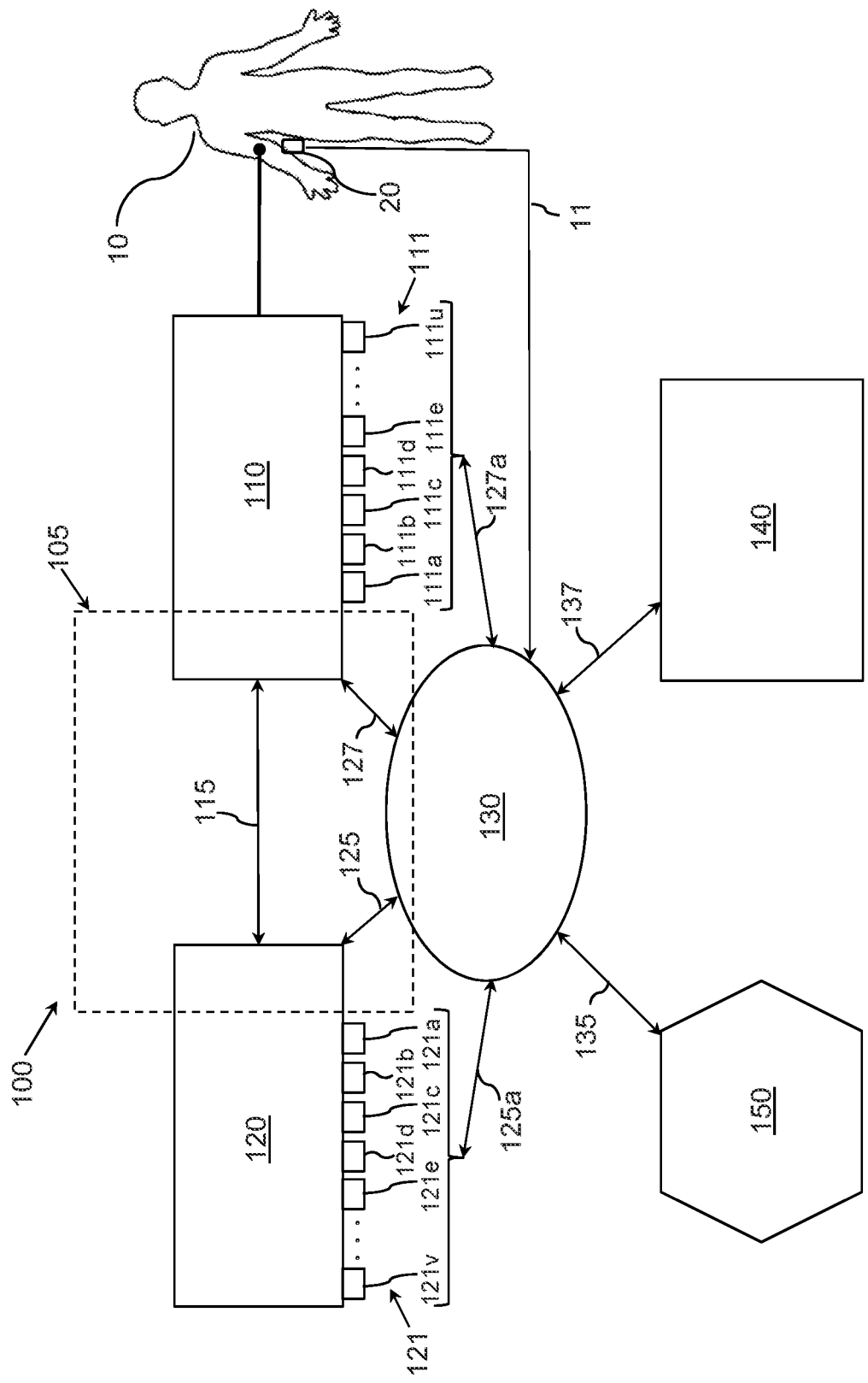
FIG. 1 illustrates an example of a configurable fluid delivery system in accordance with the present disclosure.

In a broad sense, a fluid delivery device may include a fluid delivery unit, such as a cradle element to hold a syringe, a disposable unit or fluid path element, such as a syringe, a fluid actuator unit, such as a linear driven piston and drive elements, which together are operated and controlled by a control unit to provide an injection. The control unit may present a user with information regarding setting up an injection protocol, ongoing status during the injection, and additional information regarding the injection procedure after the procedure has been completed. In one example, the information may be presented as a graphical interface specific to the type of injection protocol being used. Additionally, the control unit may receive information from the user via an input device regarding parameters necessary for setting up the injection protocol, thereby affecting the setup and operation of the fluid delivery device.

A typical design cycle for such a fluid delivery device may have separate portions dedicated to the development of the actuator unit, the fluid delivery unit, the fluid delivery path or disposable unit, and the control unit. The design of the control unit, in particular, may require detailed knowledge of the fluid delivery unit, the fluid actuator unit, and the disposable unit. The control unit may include programming to incorporate safety features to prevent any one of the components from being damaged or operated outside its design specifications. Information about such limits can be contained in the data source or sources associated with one or more of the system components and communicated to and/or from the control unit. Such safety features, such as maximum fluid delivery rate, total fluid delivery volume, and maximum fluid delivery pressure, may depend on the capabilities of the various components of the fluid delivery device. There is the "weakest link" phenomena in which system limits may need to be set according to the system component which is first to fail, for example the element with the lowest pressure rating. The control unit uses data from all the elements and the operator and builds up a system model and control strategy. Additionally, the control unit may present a graphical interface to the user specific to the type of procedure for which the fluid delivery device may be used and may be designed to provide the optimum information regarding that procedure. The graphical interface may also be designed to receive only the information relevant to that injection procedure and include safeguards to prevent a user from entering information outside the appropriate bounds for operating the fluid delivery unit during that protocol.

It may, therefore, be appreciated that significant programming may be involved in the design of a control unit. Although any one type of fluid delivery device may differ from another type of fluid delivery device, nevertheless, there may be control components that are similar across a number of devices. One method for streamlining the control unit design may be for developers to have a library of routines (re-usable code) from which specific control routines may be incorporated into the control unit software during development. A difficulty with this method of software development may lie with potential upgrades and changes to hardware components of the fluid delivery device. If hardware is replaced on a fluid delivery device that is already in operation or available for sale, novel features in the upgraded hardware may not be reflected in the original control software, and thus may go unused. Alternatively, an upgrade in the device hardware may then require an equivalent upgrade in the control unit software to take advantage of the new features.

One method of addressing possible unequal development cycles of control unit software and delivery unit hardware may include the addition of intelligence within the separate hardware components associated with the fluid delivery device. In one embodiment, each fluid delivery unit, each actuator unit, and each disposable unit may have identification information included in the hardware itself. Such identification information may then be read by the control unit as a means to identify each of the components included in the fluid delivery device. The control unit software may then use the identification information to determine which of a variety of pre-programmed steps to take. In another embodiment, some or all of the fluid delivery unit components may include not only identification information, but executable software code (for example in small flash memory units) that may be downloaded by the control unit for execution. In this manner, the original control unit programming may not be restricted to the original programming, but may be able to incorporate updated programming associated with the individual hardware components necessary. Alternatively, each of the fluid delivery unit components may include a unit-specific control unit that may present a standardized interface to the system control unit.

Disclosed below are general outlines of generic components that may be used in such an intelligent and configurable fluid delivery device and system, as well as a few specific examples of the types of fluid delivery devices that may be developed from it. It may be appreciated that a wide variety of individual devices may be produced from such a system, and that the examples disclosed below include merely a small number of possible devices. It may be further appreciated that, where a singular component—such as a fluid delivery unit, a fluid actuator unit, a disposable unit or an interface device—is disclosed, multiple components may also be considered incorporated within the scope of the disclosure.

It should be understood that various embodiments of this invention can be employed to overcome one or more of the following drawbacks or limitations of fluid delivery systems. One drawback is that most pumps have a limited accuracy range, for example two or at most three orders of magnitude of volume or flow rate accuracy. A second drawback is wasted volume in tubing. If small volumes of an expensive fluid are to be used, it is desirable to waste little of the fluid. One approach to do this uses tubing of small inner diameter (ID). But with small ID tubes, pressure drop can be significant. Another approach is to use the concentric flow approach discussed in U.S. Patent Application Publication 2011/0209764 to Uber et al., which is herein incorporated by reference, in which a small volume and flow can be placed in the center of a larger flow to carry the fluid to the recipient.

Additional items that one or more of the embodiments of this invention address include: slow rise times at the start of the delivery of a particular fluid; dribble or undesired flow after the actuator movement has stopped; backflow of one fluid into a fluid path element that should contain only a different fluid; ratio inaccuracy on the start of a simultaneous delivery; ratio inaccuracies upon the stopping or conclusion of injection(s); the inability to detect leaks; the various effects of the capacitance of various fluid path or system elements; the ability to control flow allowing for various fluids to have various viscosities; and the ability to accurately measure and control pressure to protect the recipient and/or user(s) of the fluid and the fluid delivery apparatus.

FIG. 1 illustrates a general intelligent and configurable fluid delivery system, generally designated 100. The system 100 may include a fluid delivery unit 110 and a fluid actuator unit 120 that are placed in reversible mechanical communication 115 so that the fluid actuator unit 120 may cause the fluid delivery unit 110 to express a fluid for use during a procedure. The fluid delivery unit 110 may also be in reversible communication with a control unit 130 over a fluid delivery unit communication link 127. Similarly, the fluid actuator unit 120 may also be in reversible communication with the control unit 130 over a fluid actuator unit communication link 125.

Figure 2:
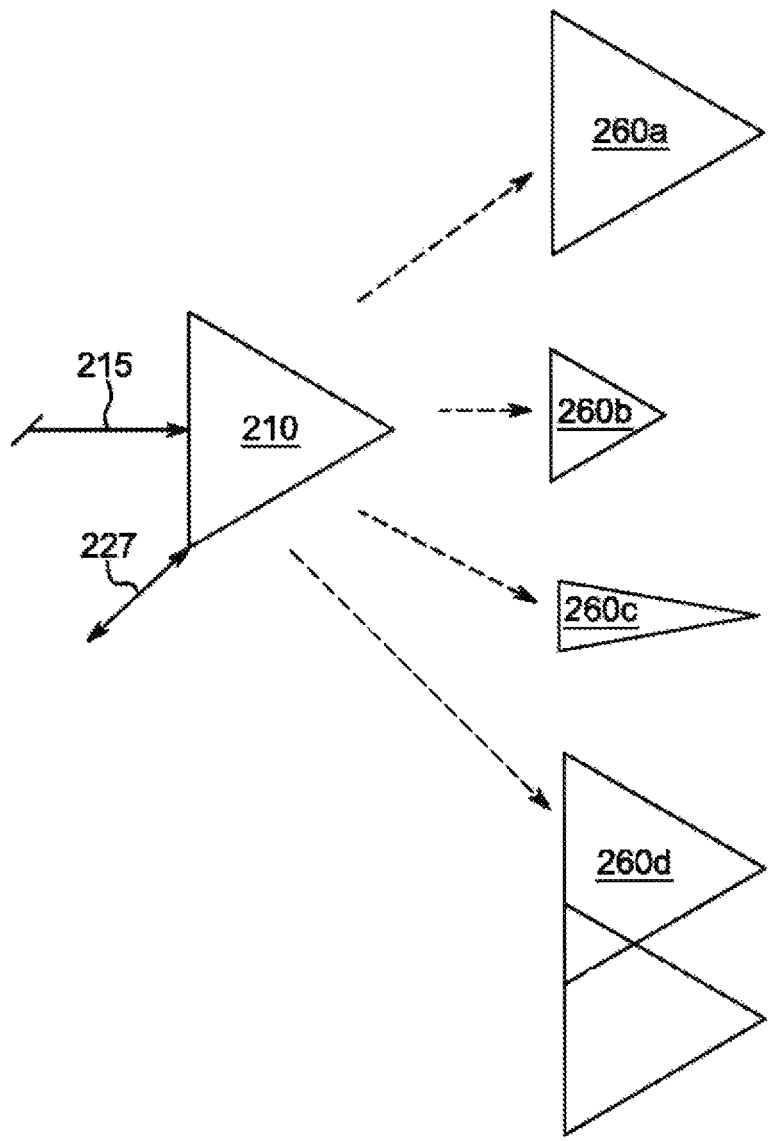
FIG. 2 illustrates examples of a fluid delivery unit that may be part of a configurable fluid delivery system in accordance with the present disclosure.

As illustrated in FIG. 2, non-limiting examples of a fluid delivery unit 210 may include one or more of the following: a single syringe delivery unit 260a, a micro-syringe delivery unit 260b, a catheter 260c, a multiple syringe delivery unit 260d, and a needle. Additional non-limiting fluid delivery units may include one or more of the following: a gear pump unit, a peristaltic pump unit, a multiple inline syringe pump unit, a diaphragm pump unit, and other pumping mechanisms known in the medical fluid delivery art.

Referring again to FIG. 1, the fluid delivery unit 110 may include at least one delivery unit data source 111. In some non-limiting embodiments, the delivery unit data source 111 may include one or more of the following: a delivery unit sensor 111a, a delivery unit ID device 111b, and a delivery unit data storage device 111c. In some other non-limiting embodiments, the delivery unit data source 111 may include one or more of the following: a delivery unit temperature sensor 111d, a delivery unit pressure sensor 111e, a motor current sensor 111f, a force sensor 111g, a delivery unit fluid flow sensor 111h, a delivery unit fluid flow acceleration sensor 111i, a delivery unit fluid flow deceleration sensor 111j, a delivery unit particle-counting sensor 111k, a delivery unit fluid viscosity sensor 111l, and a delivery unit fluid leak sensor 111m. In other non-limiting embodiments, the delivery unit data source 111 may include one or more of the following: a linear or matrix bar code 111n, a data label 111o, and an RFID device 111p. Additional non-limiting embodiments of the delivery unit data source 111 may include one or more of the following: a flash drive device 111q, a readable solid state memory device 111r, a magnetic memory strip 111s, a disk drive 111t, and a programmable/readable solid state memory device 111u. In some non-limiting embodiments, the data source(s) 111 may have two-way communication with control unit 130, for example the control system can update the data source(s) 111 with usage data so that if an element is used and then set aside, the control unit 130 can know this and act appropriately, for example by alerting the user if the time has been too long or showing the fill volume and contents if the element had been filled with a fluid at a previous time.

Delivery unit data, associated with any one or more of the delivery unit data sources 111, may include without limitation any one or more of the following: delivery unit sensor unit data, delivery unit identifier data, and delivery unit data from a delivery unit data storage device. In some embodiments, the delivery unit data may include one or more of the following: a delivery unit product ID code, a delivery unit model number, a delivery unit serial number, a delivery unit date of manufacture, a time of fluid injection, a software version identifier, a firmware version identifier, calibration data, operational capability data, and a delivery unit place of manufacture. Additional non-limiting examples of delivery unit data may further include one or more of the following: delivery unit configuration data, delivery unit use data, actuator unit compatibility data, a time of fluid injection, and delivery unit function instructional code. Descriptions of exemplary data associated with one or more fluid path elements may be found in U.S. Pat. No. 5,739,508 to Uber which is hereby incorporated by reference in its entirety.

The fluid delivery unit 110 may also be configured to be in reversible mechanical communication with a fluid path element, for example a disposable device. The disposable device may include, as non-limiting examples, one or more of the following: a cannula that may include a needle, a contrast-containing syringe, a pharmaceutical-containing syringe, a cell fluid containing syringe, a gene therapy containing syringe, a flushing-fluid containing syringe, an empty syringe, a high-pressure fluid syringe, a micro-syringe, a transfer tube, a one-way valve, a manually controllable multi-port valve or stopcock, an automatically controllable multi-port valve, and one or more pieces of tubing or conduit T's or Y's that together may form a fluid path. Alternatively, one or more fluid path elements may be reusable, either being flushed, cleaned, sterilized and/or needing no additional preparation for repeated safe use, depending upon the design and use.

The disposable device may also include, as non-limiting examples, one or more of the following: at least one disposable device identification device, at least one disposable device sensor, and at least one disposable device data storage device. The fluid delivery unit 110 may be configured to receive disposable unit data from one or more of the following: a disposable device identification device, a disposable device sensor, and a disposable device data storage device. Non-limiting examples of disposable unit data may further include one or more of the following: disposable identification data, disposable temperature data, disposable pressure data, disposable fluid leak data, and disposable multiple use data.

FIGS. 3A-E further illustrate non-limiting configurations of disposable units with associated fluid delivery units.

Figure 3A:
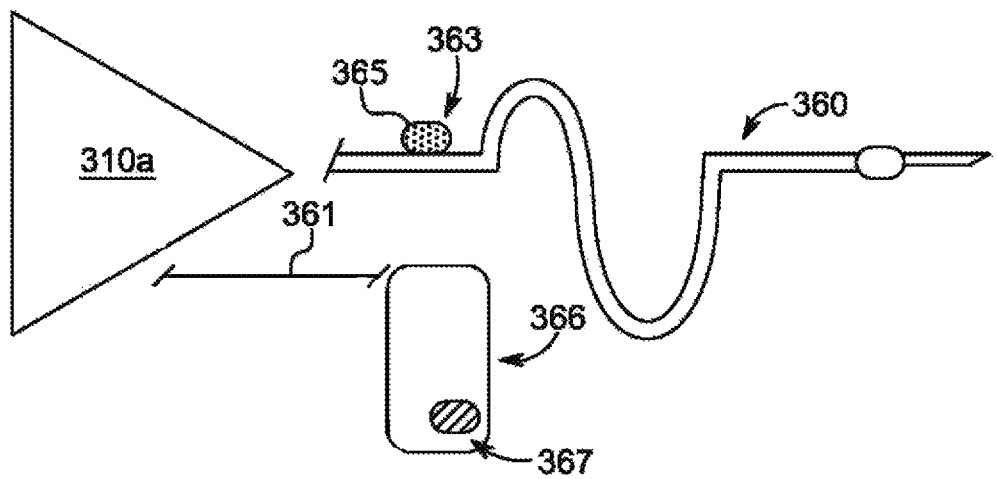
FIGS. 3A-E illustrate examples of fluid path configurations and disposable units that may be used with fluid delivery units that may be part of a configurable fluid delivery system in accordance with the present disclosure.

FIG. 3A illustrates a fluid delivery unit 310a that may be of a type capable of forming a reversible mechanical communication with a disposable tubing set 360 having a needle. The tubing set 360 may include a data source 363, such as a sensor or a device containing identification data. The data source 363 may further include a data source output 365 that may be in communication with any of the components of the fluid delivery system 100. Supply fluid for the fluid delivery unit 310a may be sourced from any of a number of fluid sources 366 over a fluid delivery line 361. Sources may include bags or vials among others such sources. The fluid source 366 may also include a data source 367, such as a sensor or a device containing identification data.

Figure 3B:
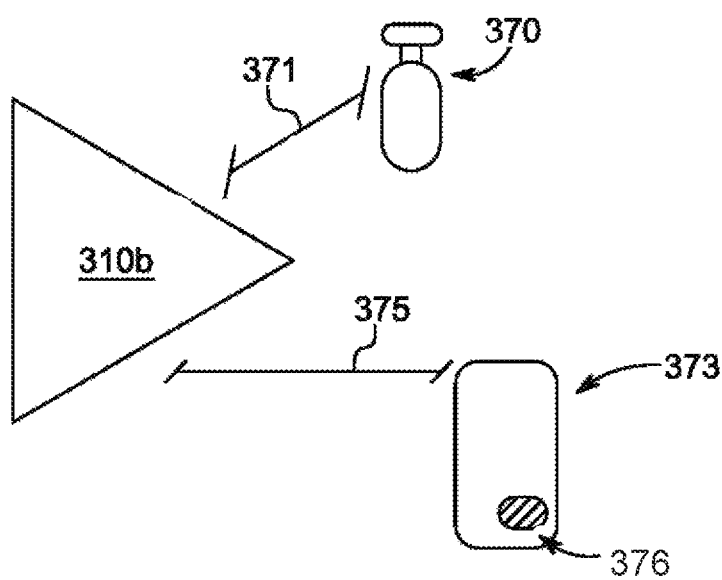

FIG. 3B illustrates a fluid delivery unit 310b that may receive different fluids from multiple fluid sources. One fluid for the fluid delivery unit 310b may be sourced from a first fluid source 370 over a first fluid delivery line 371. The first fluid source 370 may be a vial containing a small amount of fluid, such as a radiopharmaceutical fluid. The second fluid source 373 may be a bag containing a large amount of fluid, such as a fluid to purge the fluid delivery unit 310b of the radiopharmaceutical fluid. The second fluid source 373 may also include a data source 376, such as a sensor or a device containing identification data. Although not illustrated in FIG. 3B, the first fluid source 370 may also include a data source.

Figure 3C:
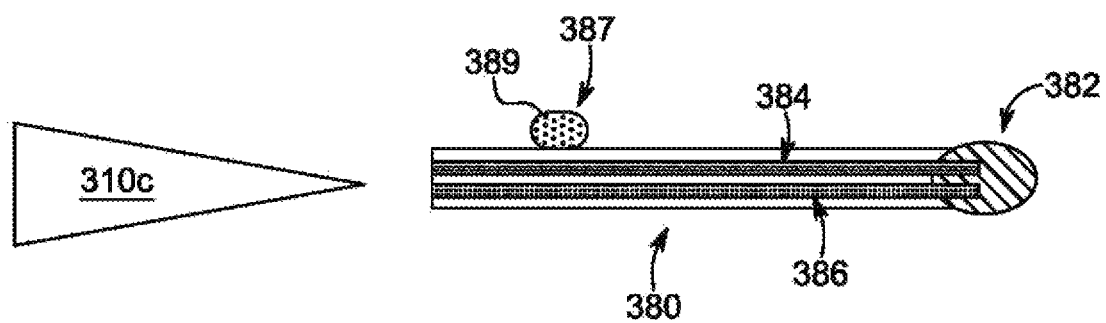

FIG. 3C illustrates a fluid delivery unit 310c that may be in reversible physical communication with a catheter 380, such as a balloon catheter. The fluid delivery unit 310c may be configured to supply fluid to the catheter 380 over an inlet line 384 and receive fluid from a return line 386. Fluid introduced into the catheter 380 may be used to inflate or deflate an angioplasty balloon 382. The catheter 380 may also include a data source 387, such as a sensor or a device containing identification data. The data source 387 may further include a data source output 389 that may be in communication with any of the components of the fluid delivery system 100.

Figure 3D:
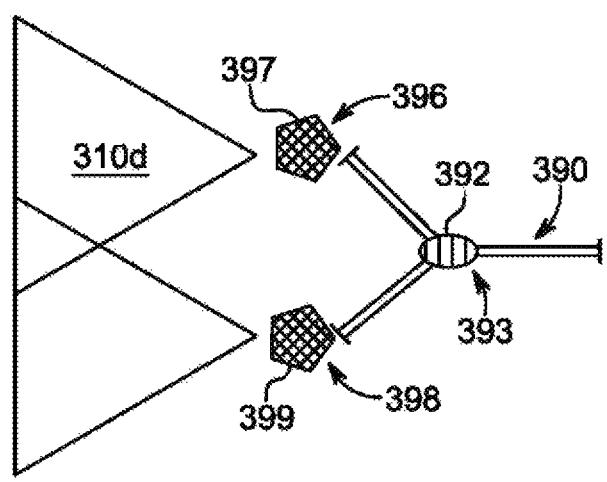

FIG. 3D illustrates a fluid delivery unit 310d that may be used to supply multiple fluids. Although FIG. 3D illustrates a single fluid delivery unit 310d that may be used to supply multiple fluids, it may be recognized that multiple fluids may be delivered by two separate fluid delivery units, such as 260a, coordinated through the communication of one or more fluid actuator units 120 and/or control units 130. Each fluid may be supplied from a separate device, such as a syringe. An example of such a device may include a fluid delivery system designed to inject a radiological contrast fluid and a separate flushing solution, such as neutral saline. In addition to the syringes supplying the fluids, disposable units may include a manifold 390 configured to receive fluid from each of the syringes. The manifold may be in fluid communication with a first syringe over a transfer line containing a first fluid control device 396, such as a first valve. The first fluid control device 396 may be self-actuating, manually controlled or under automated control by a control unit (130, see FIG. 1). One example of a self-actuating valve may be a one-way fluid or check valve to prevent fluid from flowing into the first syringe from the other syringe or another source. One example of a manual valve is a ball valve or stopcock. Automated control may be accomplished by transmission of control signals over a first valve control line 397. The manifold 390 may also be in fluid communication with a second syringe over a transfer line containing a second fluid control device 398, such as a second valve. The second fluid control device 398 may be self-actuating, manually controlled or under automated control by a control unit (130, see FIG. 1). One example of a self-actuating valve may be a one-way fluid valve to prevent fluid from entering the second syringe. Automated control may be accomplished by transmission of control signals over a second valve control line 399. The first fluid control device 396 and the second fluid control device 398 may be operated to allow only one fluid to flow at time, or may permit both fluids to flow into the manifold 390 effectively simultaneously, allowing fluid mixture. The manifold 390 will contain one or more confluences where the two or more fluid paths come together to flow on. An example of a confluence may be a simple T or Y in a tubing set. A confluence may be more complicated; configured such that it places the flow of one fluid in the middle of a second fluid flow or, alternatively, it may thoroughly mix the two fluids, as is discussed in co-pending U.S. patent application Ser. No. 13/799,426 to Schriver et al. titled "*Fluid Path Set With Turbulent Mixing Chamber, Backflow Compensator,*" which is incorporated herein by reference. A confluence may also include a selection valve 393 to select the flow of only one of the two fluids at a time, or it may be configured to act as a selector and/or combiner and/or mixing valve of the two fluids. The selection valve 393 may be self-actuating, under manual control or under automated control by a control unit (130, see FIG. 1). Automated control may be accomplished by transmission of control signals over a selection valve control line 392. If manual elements are used or other operator intervention is needed before, during, or after a fluid delivery, the control unit may direct the operator to perform the necessary action and ask for confirmation that that action has been taken, for example to move a valve or to check for air in a fluid path element. This is incorporated into its control algorithm.

Figure 3E:
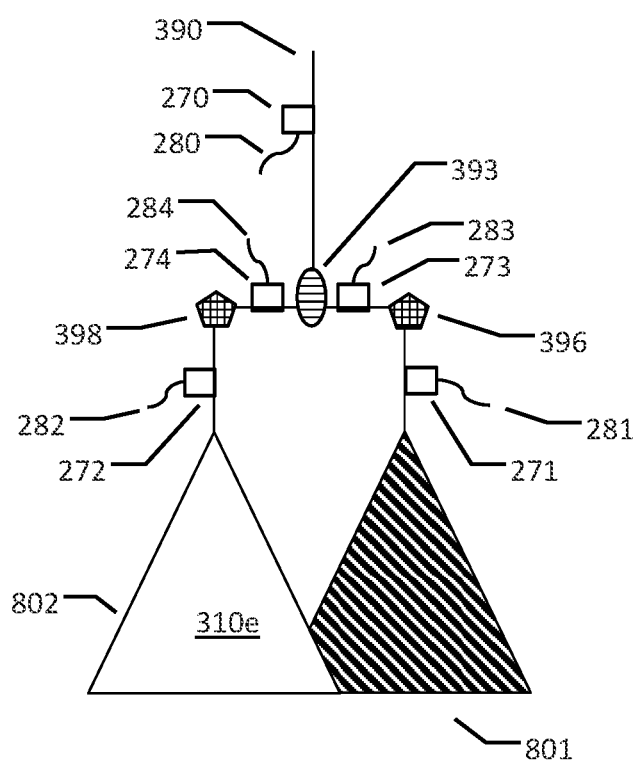

FIG. 3E represents another embodiment comprising the embodiment of FIG. 3D with the optional addition of one or more sensors 270, 271, 272, 273, and 274, which may communicate to the control unit 130 via wires or other communication means 280, 281, 282, 283, 284 respectively. These sensors may be part of the disposable fluid path elements or may be reusable and be part of fluid delivery unit 110 or the fluid actuator unit 120. The sensor may be pressure sensors, temperature sensors, air sensors, or other sensors mentioned here or used in the art. The output of these sensors may be used by the control system, either in the fluid delivery unit, the fluid actuator, or the overall control unit to assess the proper and safe operation of the system or as part of the control algorithm or program to operate the various valves and/or actuators. Examples uses of this embodiment will be discussed elsewhere.

It may be appreciated that control and/or sensor data transmitted by any of the sensors or function control devices associated with the disposable unit(s) as disclosed above may be received by any one or more of the components of fluid delivery system 100, including without limitation, the fluid delivery unit 110, the fluid actuator unit 120, and/or the control unit 130. Similarly, control and/or sensor data received by any of the sensors or function control devices associated with the disposable unit(s) as disclosed above may be transmitted by any one or more of the components of fluid delivery system 100, including without limitation, the fluid delivery unit 110, fluid actuator unit 120, and/or control unit 130. Similarly, control and/or sensor data received by the fluid delivery unit 110 from any of the sensors or function control devices associated with the disposable unit(s) as disclosed above may be transmitted to any one or more of the remaining components of fluid delivery system 100, including without limitation, the fluid actuator unit 120 and/or control unit 130.

Returning to FIG. 1, non-limiting examples of a fluid actuator unit 120 may include one or more of the following: a pump, a single-piston actuator, a multi-piston actuator, a multi-cylinder actuator, a rotary actuator, a reciprocal plunger actuator, and a peristaltic actuator. The fluid actuator unit 120 may also include at least one actuator unit data source 121. The actuator unit data source 121 may include, as non-limiting examples, one or more of the following: an actuator unit sensor 121a, an actuator unit ID device 121b, and an actuator unit data storage device 121c. The actuator unit data source 121 may further include, as non-limiting examples, one or more of the following: an actuator unit temperature sensor 121d, an actuator unit pressure sensor 121e, an actuator unit mechanical motion sensor 121f, an actuator unit fluid delivery rate sensor 121g, an actuator unit fluid delivery acceleration sensor 121h, a force sensor, a motor current sensor 121i, a syringe identification sensor 121j, an actuator unit fluid delivery particle-counting sensor 121k, an actuator unit fluid viscosity sensor 121l, an actuator unit fluid delivery deceleration sensor 121m, a valve position or actuation sensor 121n and a leak detection sensor 121o. Additionally, the actuator unit data source 121 may incorporate one or more of the following: a linear bar code 121p, a matrix bar code 121q, and an RFID device 121r. Further, the actuator unit data source 121 may include one or more of the following: a disk drive 121s, a flash drive device 121t, a readable solid state memory device 121u, and a programmable/readable solid state memory device 121v.

The actuator unit data source 121 may provide actuator unit data that may be available to one or more of the fluid delivery unit 110 and the control unit 130. The actuator unit data may include, as non-limiting examples, one or more of the following: actuator unit sensor unit data, actuator unit identifier data, and actuator unit data from an actuator unit data storage device. Additionally, the actuator unit data may further include one or more of the following: an actuator unit product ID code, an actuator unit model number, an actuator unit serial number, an actuator unit date of manufacture, a software version identifier, a firmware version identifier, and an actuator unit place of manufacture. The actuator unit data may also include one or more of the following: actuator unit configuration data, actuator unit use data, delivery unit compatibility data, calibration data, operational capability data, and actuator unit function instructional code.

The fluid actuator unit 120 may further be configured to receive and provide delivery unit data from and to one or more delivery unit data sources 111. Additionally, the fluid actuator unit 120 may be configured to be in reversible fluid communication with a fluid source.

Although mechanical communication 115 may refer solely to the arrangement of the physical components, it should be understood that the communication may also incorporate data communication between the fluid delivery unit 110 and the fluid actuator unit 120. Such data communication between the fluid delivery unit 110 and the fluid actuator unit 120 may be embodied in the same physical connector as the mechanical communication connector (such as a "plug and play" connection), or the data communication between the two units may be accomplished using one or more separate electrical connectors or other wired or wireless communication methods known to those skilled in the art. In one non-limiting embodiment, the actuator unit 120 and the delivery unit 110 may simply "snap together". In an alternative non-limiting embodiment, the actuator unit 120 and the delivery unit 110 may additionally be affixed onto a mechanical or electro-mechanical base, frame or support 105 that may assist in stabilizing the actuator unit and the delivery unit in their functional relationship. It may be appreciated that fluid delivery units 110 and fluid actuator units 120 may be designed specifically for use as part of the fluid delivery system 100. Alternatively, one or more "translation pods" may permit a commercially available fluid delivery unit 110 or fluid actuator unit 120 to be incorporated into the fluid delivery system. Such "translation pods" may include simple electronic pass-through components to permit data exchange with the control unit 130. Alternatively, the "translation pods" may include microprocessors, non-volatile and volatile storage media and other intelligent electronics along with program instructions to translate instructions issued by the control unit 130 into commands and data native to the commercial fluid delivery units 110 or fluid actuator units 120. The "translation pods" may similarly convert data from the commercial components into data and information readily usable by the control unit 130. Alternatively, a commercially available fluid delivery unit 110 or fluid actuator unit 120 may include the data and interface connections pre-configured to exchange data with control unit 130 without the need for a "translation pod". Alternatively, the "translation pod" functionality can be incorporated into or performed by the control unit 130.

It may be appreciated further that the mechanical communication 115 between the fluid actuator unit 120 and the fluid delivery unit 110 may be reversible. Such a feature may be useful if the fluid actuator unit 120 and/or the fluid delivery unit 110 suffer a failure during use requiring a replacement part to be substituted for the failed unit. A failure condition of the fluid actuator unit 120 and/or the fluid the delivery unit 110 may be communicated to the user by the control unit 130 via any of a number of possible output devices. The failure notification may be based at least in part on mechanical status data received by the control unit 130 from the fluid delivery unit 110 and/or the fluid actuator unit 120. The replacement part for either the fluid delivery unit 110 or fluid actuator unit 120 may be of the same type as the original (failed) unit, or may be of a different type such as an upgraded part.

The fluid delivery unit 110 and the fluid actuator unit 120 may further be in data communication with the control unit 130. The fluid delivery unit 110 may have a fluid delivery unit communication link 127 with the control unit 130, while the fluid actuator unit 120 may have a separate fluid actuator unit communication link 125 with the control unit. Alternatively, the fluid delivery unit 110 and the fluid actuator unit 120 may communicate with the control unit 130 over the same data communication link. The communication links may be reversible, so that the control unit 130 may both receive data from and transmit data to the fluid delivery unit 110 and/or the fluid actuator unit 120. The data source(s) 111 for fluid delivery unit 110 may also use communication link 127 to communicate with the control unit 130 or may use a separate link 127a. Similarly, data source(s) 121 for fluid actuator unit 120 may also use communication link 125 to communicate with the control unit 130 or may use a separate link 125a. Such links may be manifested in wired or wireless implementations known to those skilled in the art.

Referring still to FIG. 1, the fluid delivery system 100 of the present invention may be configured to be suitable for use in injecting one or more fluids (e.g., a contrast medium and a diluent such as saline) into a patient 10 or other recipient as part of a contrast-enhanced imaging procedure from which to obtain one or more diagnostic-quality images of the recipient 10 or one or more regions of interest thereof. In this regard, the system 100 may include one or more sensors, generally designated 20, with which to sense one or more physiological parameters of the recipient 10. The parameter(s) sensed by sensor(s) 20 may be provided as feedback to the control unit 130 or other components of fluid delivery system 100 for the purpose of assisting the system to derive an initial protocol by which the one or more fluids will be injected into the recipient 10 or to modify the injection protocol. In either case, the one or more sensor(s) 20 may be used to measure heart rate, blood pressure, pressure inside a vessel, tissue, or body cavity, blood pH, temperature, weight or other desired physiological parameters of the recipient 10. Depending upon the application, it is contemplated that sensor(s) 20 may be placed, for example, either in-vivo or external to the patient, and may be implemented as instruments separate from the sensor(s) disclosed in connection with the disposable fluid path elements discussed above. Alternatively, sensor(s) 20 may be integral to and/or embodied in the form of the sensor(s) disclosed in connection with those disposable fluid path elements.

It may be appreciated that more than a single fluid delivery unit 110 and fluid actuator unit 120 may be associated with the fluid delivery system 100. As one non-limiting example, a control unit 130 may be in data communication with a plurality of fluid delivery units 110 and associated fluid actuator units 120. Such a configuration may be useful for a veterinary research application in which a number of experimental animals are each infused with one or more medications according to a protocol specifically designed for each animal. The control unit 130 may permit a user to control and monitor each fluid delivery unit 110 separately, and provide information from each combination of a fluid delivery unit 110 and a fluid actuator unit 120.

As disclosed above, the fluid delivery unit 110 may be in reversible communication with a control unit 130 over a fluid delivery unit communication link 127. Non-limiting examples of data to be communicated may include fluid delivery unit data and/or disposable device data. Similarly, the fluid actuator unit 120 may be in reversible communication with the control unit 130 over a fluid actuator unit communication link 125. Non-limiting examples of data to be communicated may include actuator and/or control signals to activate the fluid actuator. Some non-limiting examples of such control signals may include one or more of the following: a fluid delivery unit rate signal, a fluid delivery unit volume signal, a fluid delivery unit pressure signal, a fluid delivery unit particle-counting signal, and a fluid delivery unit acceleration/deceleration signal. In addition, the control unit 130 may receive input data over an input communication link 137 from an input device 140, and provide output data over an output communication link 135 to an output device 150. It may be appreciated that the input device 140 and the output device 150 may be the same physical device. Consequently, the input communication link 137 and the output communication link 135 may be the same physical device or wireless link.

Control unit 130 may include any number of components. In some non-limiting embodiments, the control unit may include a non-transitory, computer-readable storage medium in operable communication with a computing device. In some embodiments, the control unit 130 may also include the output device 150 in operable communication 135 with the computing device as well as the input device 140 in operable communication 137 with the computing device. Alternatively, one or both of the output device 150 and the input device 140 may be separate devices from the control unit 130. Additionally, the control unit 130 may include any one or more of the following: an internet communication interface, a serial communication interface, a parallel communication interface, a local network interface, a wide range network interface, an optical interface, a wireless communications interface, a gesture-driven interface, a voice-activated interface, and an RF interface. Such communication interfaces may be in communication with, as non-limiting examples, hospital information systems (HIS), radiology information systems (RIS), imaging systems, workstations, Picture Archiving and Communication Systems (PACS), and service or monitoring systems. Non-limiting examples of output devices 150 may include: a computer, a work station, a laptop computer, an iPad, a tablet, a phablet, a Blackberry device, a PDA, and a cellular telephone. Non-limiting examples of input devices 140 may include: a keyboard, a mouse, a joystick, an optical character reader, an RF device interface, a voice recognition interface, a touch screen, and a motion tracking device.

The non-transitory, computer-readable storage medium, in operable communication with a computing device as part of the control unit 130, may contain one or more programming instructions that, when executed, cause the computing device to: receive delivery unit data from the delivery unit data source(s) 111 and actuator unit data from the actuator unit data source(s) 121; determine a mechanical compatibility status between the fluid delivery unit 110 and the fluid actuator unit 120 based, at least in part, on the delivery unit data and the actuator unit data; transmit, to the output device 150, an output related to the mechanical compatibility status; determine a communication integrity status between two or more of the fluid delivery unit 110, the fluid actuator unit 120, and the control unit 130; and transmit, to the output device 150, an output related to the communication integrity status. In addition, the one or more programming instructions may cause the computing device to transmit, to the output device 150, an output configuration for the fluid delivery system in a user understandable form, such as on a graphical display. The output configuration is preferably dependent, at least in part, on one or more of the delivery unit data and the actuator unit data. The output display information may be chosen by the control unit 130 from among display data preloaded in the non-transitory memory. In one non-limiting embodiment, the specific display may be based at least in part on the fluid delivery unit data, the disposable data, and/or the fluid actuator data. In another non-limiting embodiment, the specific display may be based at least in part on a procedure entered by the user via the input device 140. Alternatively, a user may choose a specific display from a library of displays. In another embodiment, a user may create a custom display from graphical primitives provided by the control unit 130.

It may be appreciated that the control unit 130 may also receive programming instructions specific to the fluid delivery unit 110 from one or more delivery unit data sources 111. Similarly, the control unit 130 may receive programming instructions specific to the fluid actuator unit 120 from one or more actuator unit data sources 121. In yet another alternative, the control unit 130 may receive programming instructions over a communications link from another device including, but not limited to, a computer, a laptop, a tablet, a cell phone, or any other source of electronic data. Additional data related to the fluid delivery unit 110, disposable devices, the fluid actuator unit 120, or any other component of the fluid delivery system 100 may be received by the control unit 130 over a communications link from another device including, but not limited to, a computer, a laptop, a tablet, a cell phone, or any other source of electronic data. Such additional data may include without limitation software or firmware upgrades for any of the components of fluid delivery system 100 or information related to user displays.

The computing device, along with its associated volatile and non-volatile storage media, may additionally serve to retain, track, organize, analyze, and log performance and/or activity data from any of the components of fluid delivery system 100. Such performance and/or activity data may be downloaded by a user at the fluid delivery system 100 or remotely. Locally downloaded performance and/or activity data may be presented to the user as part of a user display on the output device 150 or as hard copy. In some embodiments, a user may further enter instructions over the input device 140 or remotely cause the computing device to analyze the performance and/or activity data according to a user directed method. In some non-limiting examples, the computing device may include a library of possible analysis or reporting routines from which the user may choose.

It may be appreciated that control unit 130 may represent a single device or may represent multiple devices among which the various functions of the control unit as previous disclosed may be dispersed. For example, if a standalone fluid delivery system is used as fluid delivery unit 110 and/or a fluid actuator unit 120, the standalone fluid delivery system may already include some internal control functions as well as some user interface and data communication capability. Thus, control unit 130 may include higher level control functions capable of controlling and communicating with such independent units. The functions of control unit 130 may include coordinating the actions of such independent units by receiving from or transmitting to them the data and/or other information to coordinate their activities.

In addition, if the fluid delivery unit 110 and/or fluid actuator unit 120 lack real time or sufficient or continuous safety checks to confirm proper and safe delivery of the fluid to the patient, such safety checks may be included among the functions of the control unit 130 or of the "translation pods." If the fluid delivery unit 110 and/or fluid actuator unit 120 are incorporated onto the base 105 as disclosed above, the base may also include one or more safety checking functions. Such safety checking may be performed, for example, by an independent computer system incorporated in the base 105. The base 105 may be adapted to communicate with fluid delivery unit 110, fluid actuator unit 120, and/or the control unit 130. Alternatively, for configurations lacking a base 105, the control unit 130, on detecting unsafe operation during an injection, may instruct the fluid delivery unit 110 and/or fluid actuator unit 120 to stop delivery via electronic or software commands. In one alternative non-limiting example, the control unit 130 may remove power from the one or more failing units so that their operations cease. As mentioned, there are various levels of control unit functions, for example from user input and supervisory programming and operational safety checks to motor servo control and valve actuation. These functions may be distributed among various computing or control capabilities, among a central control unit, and/or among computing capabilities in the fluid actuators unit(s), the fluid delivery unit(s), the fluid path element(s), the base, and/or external computer(s) or device(s). Optionally, there may be no central control unit and the higher functions can be performed on a self-check and peer-to-peer check basis.

Figure 4:
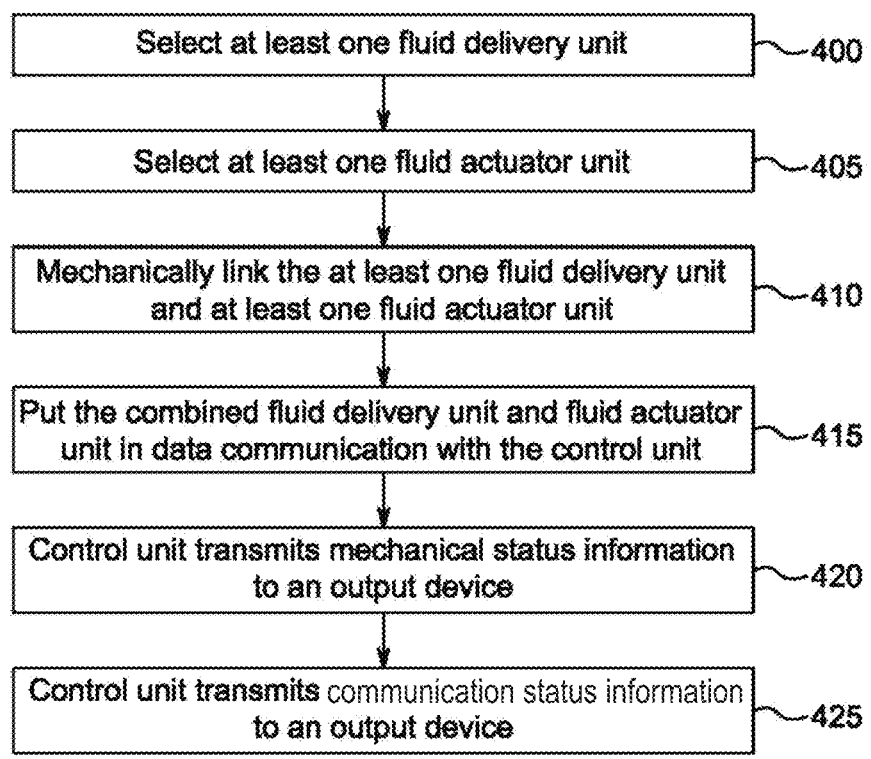
FIG. 4 is a flow diagram of an illustrative method of assembling a configurable fluid delivery system in accordance with the present disclosure.

FIG. 4 is a flow diagram of a non-limiting method in which a configurable fluid delivery system may be assembled. A user of the system may select 400 one or more of a plurality of fluid delivery units and select 405 one or more of a plurality of fluid actuator units. The user or assembler may choose either the delivery unit or the actuator unit first depending on the user criteria, such as the type of procedure for which the fluid delivery system may be used including, without limitation, a medical procedure, a veterinary procedure, or a research procedure. The user may mechanically connect the fluid actuator unit to the fluid delivery unit 410. In the spirit of the system being disclosed, it may be appreciated that the mechanical connection may be reversible. Such a reversible mechanical connection may permit the assembled units to be disassembled to replace incorrect, inoperable, or faulty units or to be reassembled in an alternate configuration for use in alternative procedures.

The user may place 415 a control unit in reversible data communication with the one or more fluid delivery units and/or actuator units. Again, it may be appreciated that the method and components associated with the communication of data among the fluid delivery unit, the fluid actuator unit, and the control unit may allow the data communication to be initiated, maintained, and dissociated. It may be understood that the order of the assembly process is not limiting. In one non-limiting alternative order of steps, the control unit may initially be connected to the delivery unit first, and then the actuator unit may be connected to the delivery unit and the control unit.

Once the three units are connected together, both mechanically and electronically, the control unit may transmit 420 mechanical status data related to the reversible mechanical communication between the fluid actuator unit and the fluid delivery unit to an output device. The control unit may also transmit 425 communication status data to the output device. The communication status data may be related to the reversible data communication between the fluid delivery unit and the control unit, and/or the fluid actuator unit and the control unit.

Given the configurable nature of the fluid delivery system, it may be appreciated that the output transmitted by the control unit related to the mechanical status data may be in a format determined at least in part on (i) fluid delivery unit data received by the control unit and/or (ii) fluid actuator unit data received by the control unit. Thus, as a non-limiting example, a graphical user interface (GUI) presented by the output device may be determined by the type of fluid delivery unit and/or the actuator unit, indicating status information specific to one or more of the units. Similarly, the output transmitted by the control unit related to communication status data may be in a format determined at least in part on (i) fluid delivery unit data received by the control unit and/or (ii) fluid actuator unit data received by the control unit. There is a benefit to the common or standard user interface employing even more graphical or diagrammatic indications of connection and interaction, with specific data being hidden but accessible on lower levels of the user interface. There could be a safety (and usability) benefit to using graphics to indicate the status of various fluid delivery units, fluid actuators, and/or fluid path elements, for example graphics of a mouse, a pig, a monkey, or a human associated with specific units or components approved for those different uses. There is also a benefit to employing user-customizable graphics in the user interface.

The method may also include a user selecting a disposable unit and placing the disposable unit in reversible mechanical communication and data communication with one or more fluid delivery units. Alternatively, the user may enable the disposable unit to be in reversible data communication with the actuator unit or with the control unit via, for example, the fluid delivery unit(s). It may further be appreciated that the control unit may transmit to an output device the mechanical status data related to the reversible mechanical communication between the disposable unit and the fluid delivery unit, or alternatively it may query the user to confirm the mechanical or other status information about the components of the fluid delivery system that the control unit 130 cannot automatically sense. In addition, the control unit may transmit to an output device communication status data related to a reversible data communication between the disposable unit and one or more of the fluid delivery units, the fluid actuator unit, and the control unit, depending on the unit receiving the communication data from the disposable unit. As one example of the use of the output status data by a user, the mechanical status data displayed on the output device may indicate a fault in the mechanical, fluid path or data connectivity between the fluid delivery unit and the actuator unit. As a result, the user may attempt to repair a faulty mechanical, fluid path or data connection by altering the appropriate connection between the fluid delivery unit and the fluid actuator unit.

Figure 5:
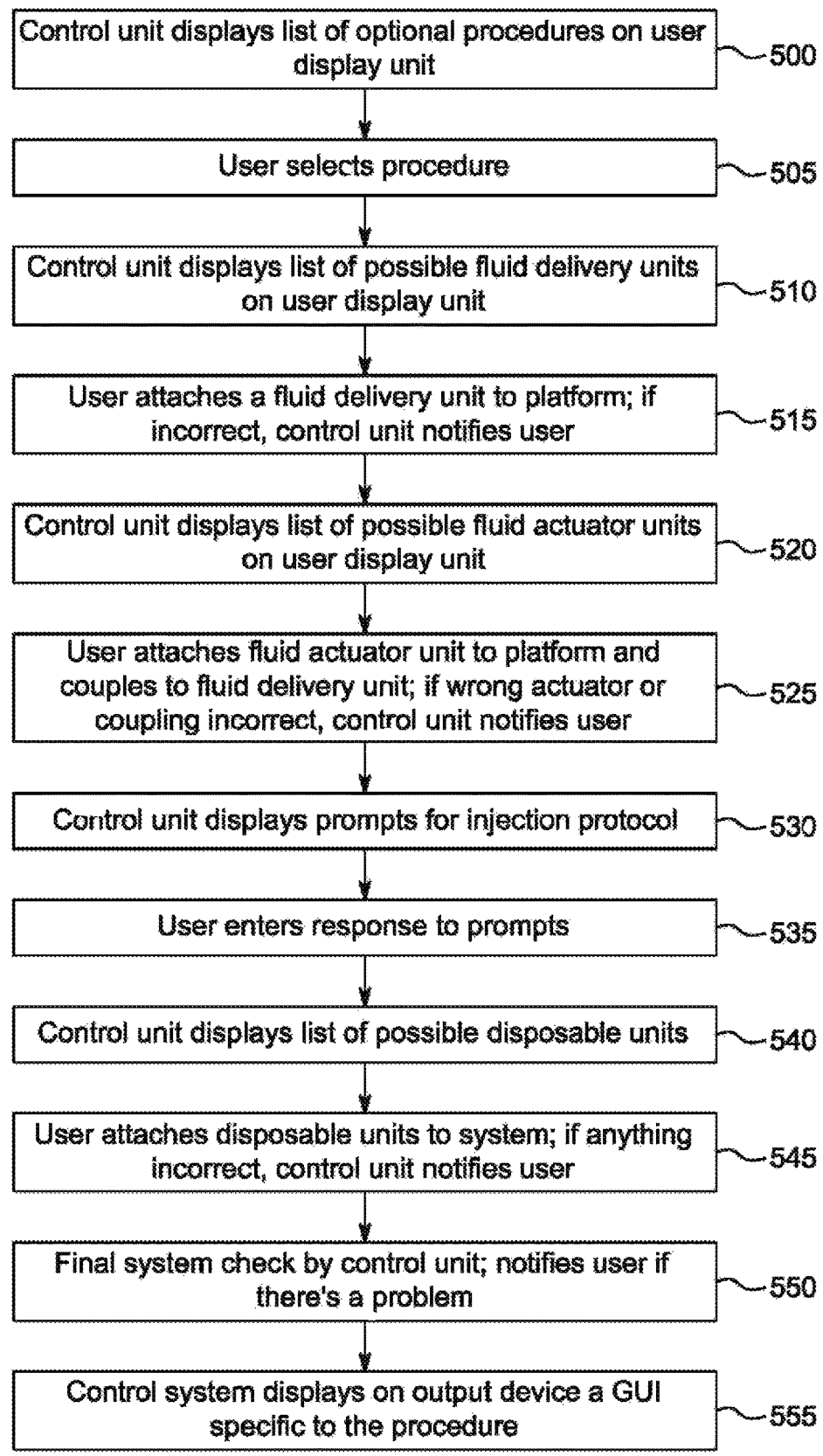
FIG. 5 is a flow diagram of an illustrative method by which a configurable fluid delivery system may assist a user in assembling the configurable fluid delivery system in accordance with the present disclosure.

FIG. 5 presents a flow chart of one embodiment of how the present invention may assist a user in configuring a specific fluid delivery system. The control unit may display 500 to the user a list of possible procedures. The list can be based upon or derived from one or more of the following: all possible procedures, preferably in a hierarchy for easy understanding and selection; currently connected units; the entire set of units available to the users; the list of units which the user has inputted as available, and a list of units from a user modifiable history of the units with which this control unit has interfaced. The user may select 505 one of the procedures representing the type of procedure the user wishes to pursue. The control unit may display 510 a list of fluid delivery units appropriate for the procedure on the output device. If the configurable system includes a mechanical or electro-mechanical base, the user may attach a fluid delivery unit to the base. The control unit, in data connection with the installed fluid delivery unit, may receive the fluid delivery unit data to determine if the unit is acceptable for the procedure. If not, the control unit may notify 515 the user that the unit is unacceptable. If the system is unable to confirm that the fluid delivery unit is attached and interfaced properly in all aspects with the control unit, the control unit may query the user to verify that the fluid delivery unit is in all aspects properly attached and interfaced.

The control unit may display 520 a list of possible fluid actuator units to the user according to the chosen procedure. The user may choose an actuator unit and couple it to the fluid delivery unit. The control unit, in data connection with both the installed fluid delivery unit and fluid actuator unit, may receive the fluid delivery unit data and fluid actuator data to determine if the actuator unit is appropriate for the delivery unit and is correctly mechanically attached to it. Again, the control may notify 525 the user if the actuator unit is improper or if the mechanical connection between the two units is faulty. If the system is unable to confirm that the fluid actuator unit is attached and interfaced properly in all aspects to ensure proper operation of the delivery unit, the actuator unit and the fluid delivery system, the control unit may query the user to verify that the fluid actuator unit is in all aspects properly attached and interfaced. It may be understood that the order of attachment of the fluid delivery unit and fluid actuator unit to the base and/or the control unit may be arbitrary.

Once the delivery unit, actuator unit, and control unit are assembled, the system may use the data from the user (type of procedure) and the delivery and actuator units to display 530 one or more possible pre-programmed fluid delivery protocols. In one embodiment, the user may respond to the protocol prompts generated by the control unit and enter 535 one selected from the list. In one alternative embodiment, the user may wish to program a new protocol based on the procedure and assembled components. Such a protocol may be entered by the user into the control unit by means of any of the above disclosed input methods. The control unit may display 540 on the output device a list of possible disposable units consistent with the procedure, delivery unit, actuator, and protocol information previously provided. The user may attach a disposable unit to the delivery unit. Data from the delivery unit, available to the control unit, may be checked by the control unit for applicability. As previously described, the control unit may notify 545 the user if the disposable unit is inappropriate for the application or if the disposable unit is not in proper mechanical contact with the fluid delivery unit. If the system is unable to confirm that the disposable unit is attached properly in all aspects to ensure proper operation of the fluid delivery unit, the actuator unit and the fluid delivery system, the control unit may query the user to verify that the disposable unit is in all aspects properly attached.

At the end of the mechanical and data connection sequence, the control unit may provide a final system-wide check to assure that an appropriate delivery unit, actuator unit, and disposable unit have been chosen by the user and have been correctly assembled. The control unit may notify 550 the user of any mechanical or electronic faults in the completed assembly. After the fluid delivery system has been assembled and tested, the control unit may display 555 on the output device an output, such as a GUI, to the user that may be specific to the procedure, components, and protocol as assembled by the user.

To aid in understanding the benefits of this invention, it may be considered somewhat analogous to constructing a desktop personal computer (PC) from various components. There is the base which has some similarities to the motherboard. The central control unit may be similar to the main processor, memory and software. The fluid actuators units could be analogous to plug-in cards. The fluid delivery unit could be a card that plugs into the fluid actuator unit or into the base itself. The disposables or fluid path elements may connect to the fluid delivery unit. In some instances, the fluid actuator unit could come with the fluid delivery unit already incorporated and fixed therein. Alternatively, the fluid delivery unit and at least some fluid path elements could come preassembled and fixed. Alternatively, a fully functioning pump with all of its independent components may be made mateable with this configurable system and be under the control of an overarching control unit to allow more sophisticated procedures than it could do by itself. Similar to the PC, the configurable fluid delivery system 100 of this invention may be designed to accommodate units or elements manufactured by various companies provided they utilize a minimum standard for at least communications and data handling. (For inexpensive, disposable or non-controlled elements, the key is fluid-tight sealing, and the data communications may be rendered optional because the user can enter the relevant data.) As in the PC analogy, different add-ins can have very different levels of sophistication and function, from a simple hard drive to a fully stand-alone tablet such as an iPad.

EXAMPLES

As one non-limiting example, the configurable system may be used to assemble a dual-injection device, composed of two syringes, each associated with a syringe drive actuator. Such a dual-syringe system is schematically presented in FIG. 3D.

A challenge associated with fluid delivery using a flexible injection system of this invention that delivers multiple fluids is that when the system and fluid path is being pressurized during the delivery of a first fluid, that first fluid may drive other fluids in a reverse flow direction, even if their pressurizing means are designed to resist or prevent movement. This reverse flow may be caused by mechanical capacitance, defined as C=V/P. The capacitance is defined as the volume change that occurs in the unit or fluid path element for a given pressure change to the fluid in that unit or element. As the capacitance, C, increases, a volume change, V, for a given pressure, P, also increases. Metal components tend to have significantly less capacitance than plastic components. However, many disposable fluid path elements are plastic because of other benefits that plastics may provide. In addition, tubing, syringe barrels, and rubber covers may also have significant capacitance.

In FIG. 3D if the fluid path 390 does not contain valves 396 and 398, when a first syringe moves forward to develop pressure to drive the fluid from the first syringe, the pressure may cause the fluid to pressurize the outflow end of the second syringe, and may even drive fluid from the first syringe into the second syringe.

One embodiment to reduce or essentially eliminate this reverse flow is to include valves 396 and 398. In this embodiment, valves 396 and 398 may be one-way or check valves that allow flow in one direction with a relatively low pressure drop. However, when only a partial volume of the syringe or fluid is to be delivered, undesirable behavior may result even with check valves. When the first syringe moves to pressurize the first fluid, a pressure is developed along the fluid path. With check valve 396 in place, the pressure drives little or no fluid into the second line. The first syringe builds up the pressure necessary to push the fluid out of the syringe and through the fluid path 390. When the second fluid is to follow or flush the first fluid, the first syringe stops moving, and the second syringe begins to move. When the pressure in the second line becomes sufficiently greater than the pressure in the first line, fluid will flow through check valve 396. At this point in the delivery, both syringes may be pressurized, but only the second fluid may flow. When fluid delivery is complete and the syringes stop their motion, the pressure in the fluid path 390 may decrease as the fluid exits the disposable unit into the patient. As long as a pressure difference exists, fluid may continue to flow or dribble out of the two syringes into the fluid path and possibly into the patient. This additional flow may result from the capacitance of the syringes and/or other fluid path elements. Disposable syringes have particularly high capacitance due to the rubber covers. Long lengths of flexible disposable tubing may also have a relatively high capacitance. One solution is to incorporate valves 396 and 398 having a high opening or cracking pressure that may be above or near the maximum operating pressure of the system. One embodiment of such a high cracking pressure valve may include a spool valve having an internal sliding element that can block fluid flow. The valve may include a resistive force element, such as a spring or a pressurized bladder, to resist the movement of the sliding element. A high crack pressure valve of the spool type is discussed below in connection with FIGS. 6A, 6B.

Figure 6A:
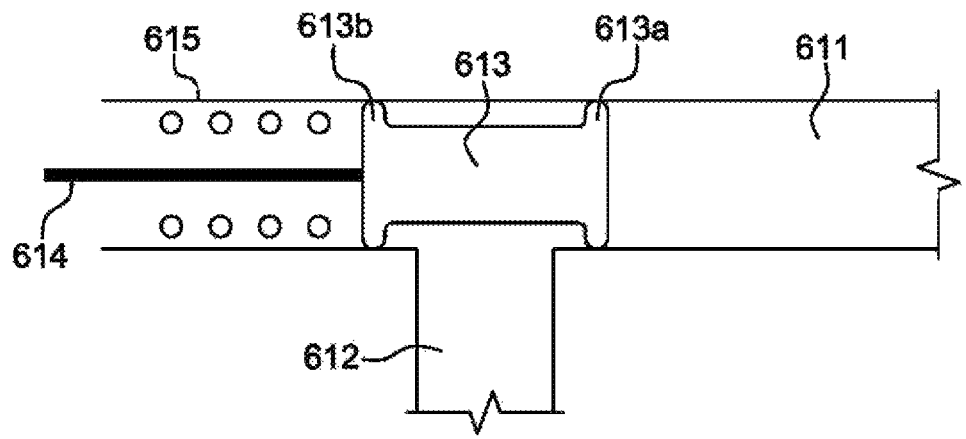
FIGS. 6A and 6B illustrate examples of a spool-type high crack pressure valve in accordance with the present disclosure.
Figure 6B:
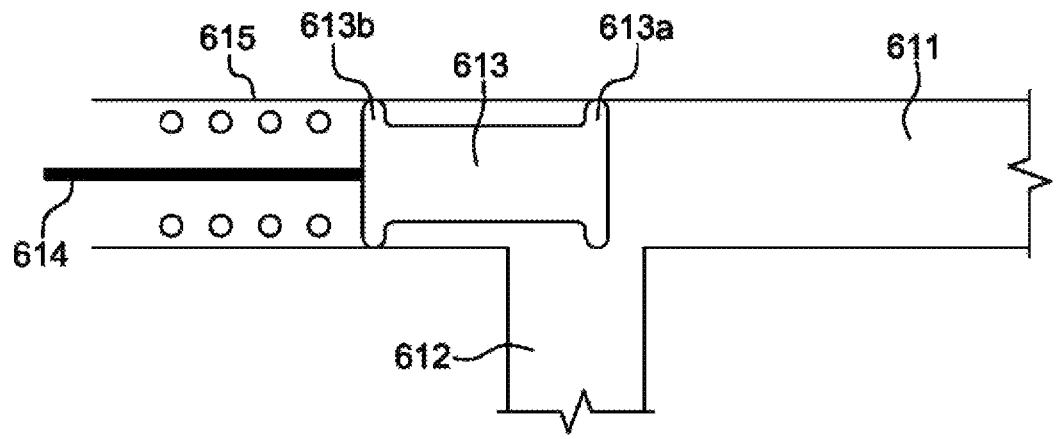

In operation, as FIGS. 6A and 6B suggest, when the fluid pressure against the sliding element is greater than the force from the force element, the sliding element may move to open an exit segment of the valve, thereby permitting fluid flow. When the pressure against the sliding element drops below the pressure required to counter the force element, the sliding element may return to its original position, thereby preventing fluid flow through the valve. In non-limiting examples, the sliding element may be made of rubber or a thermoplastic elastomer. The force element may be a metal spring or also be an elastomer, which may be manufactured as an integral part of the sliding element.

Figure 8A:
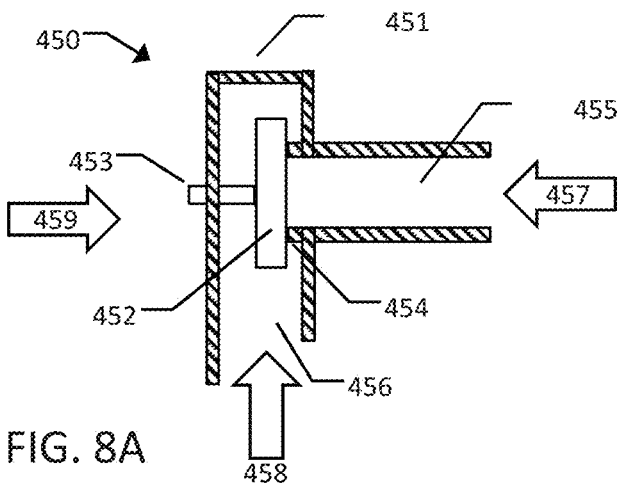
FIG. 8A-8F illustrate alternative embodiments of the valves of the present disclosure.
Figure 8B:
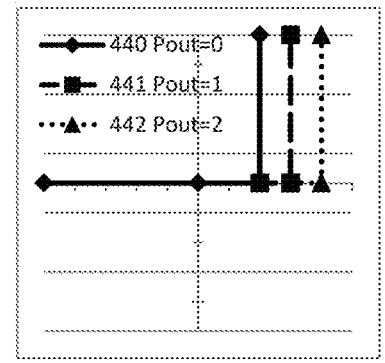
Figure 8C:
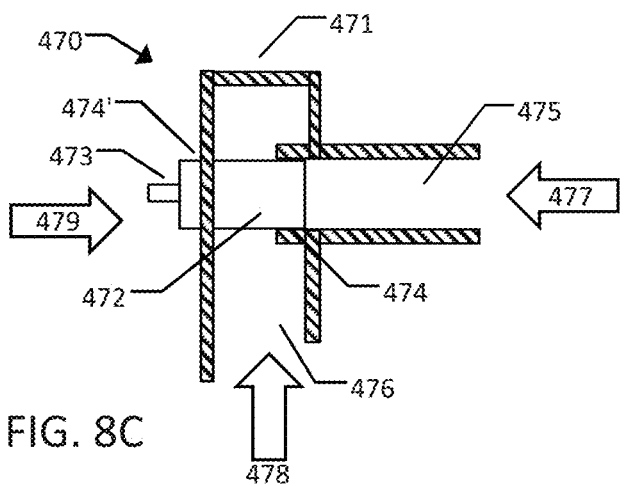
Figure 8D:
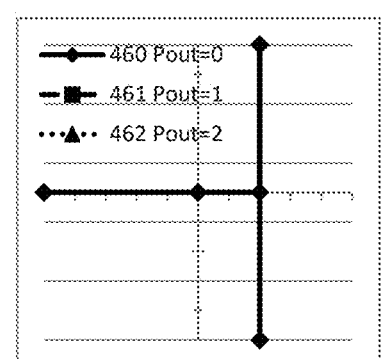

A second non-limiting embodiment may be composed of a compressible tube and an asymmetric pressure element to compress the tube. The asymmetric pressure element may be designed to compress the tube completely at one segment, compress the tube partially at a second segment, and not compress the tube at a third segment. The force of compression can be created by a variety of methods including, for example, a spring, a bladder, an electromechanical actuator, or a magnetic actuator. This configuration may be reusable with successive fluid path elements being placed in the assembly, or the spring and the pressure element may be a part of a simple clamp-on plastic or metal component that is placed on a section of tubing and discarded with the tubing. As the pressure in the third segment increases, the downward force of the pressure element may be counteracted by the fluid pressure in the second segment. An increase in fluid pressure may result in the force of the pressure element at the first segment being overcome, and fluid may flow through the valve. An example of a compression-type high crack pressure valve and its performance is shown in FIGS. 8C and 8D.

In yet another embodiment, valves 396 and 398 may be actively controlled by the control unit 130 by means of control data transmitted by the control unit over lines 397 and 399, respectively. The control unit may adjust the state of either or both of valves 396 and 398 based on data received from one or more pressure sensors associated with the disposable unit. In one non-limiting embodiment, for example as shown in FIG. 3E, such pressure sensors may be disposed with one upstream of each valve, 271 and 272, respectively, and optionally one downstream of each valve, 273 and 274, respectively. It may be appreciated that the cracking pressure to open automated control of valves 396 and 398 may be configured by the control unit, and may be adjusted according to the procedure and protocol for which the device may be used. In one non-limiting embodiment, the valves 396 and 398 are on-off valves and the control unit rapidly opens and closes them to maintain the pressure at the proper control point to simulate a high crack pressure valve. Alternatively, the valves 396 and 398 may be proportional valves which the control unit activates and controls to maintain the pressure at the proper control point. It may be recognized that an actively controlled valve has the benefit that it may be controllably opened during the preparation stage for filing or other fluid movement as well as when appropriate to relieve the pressure in the syringes when the procedure is completed. Alternatively, pressure can be relieved mechanically if the syringe piston or actuator is moved in the reverse (i.e. non-dispensing) direction. In yet another alternative example, a stopcock or other manually controlled valve (not shown) may be used in association with valves 396 or 398 for filling and/or to bleed off the pressure. In still another alternative example, the valve 396 may incorporate a mechanical lever, rod, or handle to allow for manual or automatic actuation for filling and/or to release the pressure.

In a non-limiting example, a high crack pressure valve may be placed in the fluid path from the fluid delivery unit 110, which may include a bellows or collapsible syringe or container. Descriptions of exemplary collapsible syringes and/or bladders may be found in U.S. Patent Application Publication No. 2013/0281940 to Gelblum et al., U.S. Patent Application Publication No. 2012/0209111 to Cowan et al., and International Patent Application Publication No. WO2012/061140 to Cowan et al., each of which is hereby incorporated by reference in its entirety. In syringes of this type, the syringe capacitance may be increased and the volume and flow vs. displacement can be variable and non-linear as a result of the folds of the bellows or flexibility of the collapsing member or rolling diaphragm. When the bellows syringe is operated at low pressure, the relationship between piston position and output of fluid may have one functional relationship. When the bellows is being maximally compressed by operating with a pressure at or near its maximum capability, the folds may significantly distend or distort before a significant amount of fluid is dispensed. Thus, the relationship between piston position and output of fluid may have a very different functional relationship. For discharge pressures that are intermediate between these two, the amount of collapse may be intermediate and the functional relationship between piston position and output of fluid will have a different functional relationship as well. It may be difficult to accurately or reproducibly determine the relationship between the amount of motion of the syringe plunger and the amount of fluid delivered. Accurate and consistent control of fluid delivery may require a consistent relationship between piston or pump motion and fluid volume delivery. If the syringe discharges the fluid through a high crack pressure valve, the pressure on the fluid container may be more repeatable and known. Thus, a known relationship between piston or pump motion and fluid volume may be used by the control unit 130 to accurately and consistently provide the desired fluid delivery.

A first embodiment of a high crack pressure valve, such as valve 396 in FIG. 3D, is illustrated in FIGS. 6A-6B. The fluid path segments 611 and 612 serve to conduct fluid to and from the valve, respectively. The valve further comprises a moving (in this case, sliding) element 613 which may block fluid flow between segment 611 and 612. Pressure in segment 612 cannot move the moving or sliding element 613 because the force created by the pressure acts symmetrically. The seals 613a and 613b may prevent the leakage of fluid into or out of segment 612. Pressure in segment 611 may generate a force which pushes the sliding element 613 to the left as illustrated in FIG. 6B, allowing fluid to flow from segment 611 into segment 612. The force from pressure in segment 611 may be resisted by a force element 615, such as a spring, a pressurized bladder, or an electromechanical or magnetic force actuator. Force element 615 may push sliding element 613 to the right. The motion of the sliding element 613 may be constrained to move between the closed position shown in FIG. 6A and the open position shown in FIG. 6B. Movement may be constrained by detents on the inside of the valve (not shown) or by constraints imposed by rod 614 or force element 615. The movement constraints and/or preloading have the benefit of reducing the amount of sliding/movement of element 613 which reduces system capacitance.

In operation, when the pressure in segment 611 reaches a value of P-open, the force on element 613, due to the fluid pressure being greater than the force from the force element 615, may cause the element 613 to move to the left, opening the exit segment 612 and allowing fluid to flow through the valve. When the pressure in segment 611 drops below P-open, the element 613 may move to the right and fluid flow out of or into segment 611 may be prevented.

In the case where this valve is used in a medical device, the fluid path elements may be made from plastic, such as polycarbonate or PVC. The element 613 may be made of rubber or a thermoplastic elastomer. The force element 615 may include a metal spring or an elastomer, or optionally made as an integral part of the element 613. For use in sterile situations, this design may require that all the elements that contact the fluid be sterilized or be disposable.

Figure 7:
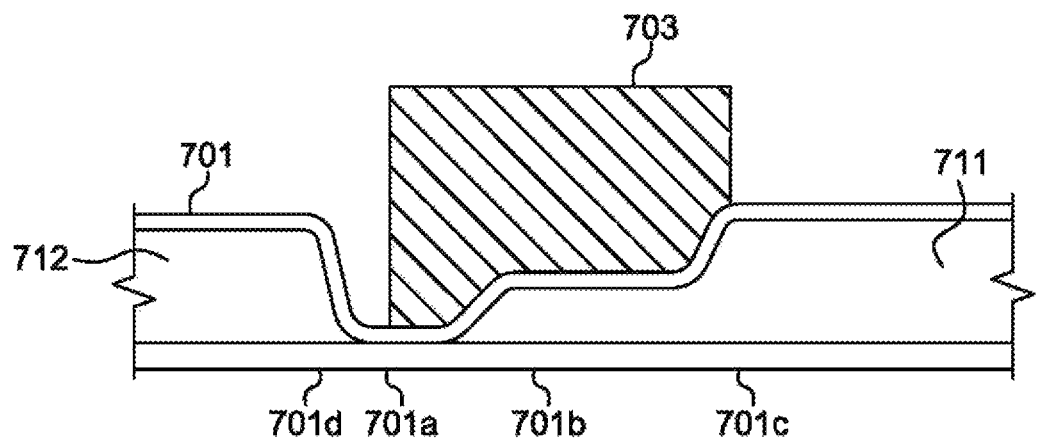
FIG. 7 illustrates an example of a compression-type high crack pressure valve in accordance with the present disclosure.

A second embodiment of a high crack pressure valve, such as valve 396 in FIG. 3D, is illustrated in FIG. 7 in which only a compressible fluid path element 701, e.g., a tube, may be in contact with the fluid and thus may be disposable. The other components of the valve can be used multiple times. Pressure element 703 may compress tube 701, closing it off at segment 701a. Pressure element 703 may be designed so that as it closes off segment 701a, it partially compresses segment 701b and does not compress segment 701c. The force of compression can be created by a variety of methods, including, for example, a spring, bladder, electromechanical, or magnetic actuator. As the pressure increases in inflow segment 711, the downward force on pressure element 703 may be counteracted by the fluid pressure in segment 701b. When the net force is such that the pressure element 703 cannot hold the tubing in segment 701a in a closed position, the tubing opens and fluid begins to flow from inflow segment 711 to outflow segment 712. This may occur at pressure P-open. When the pressure in inflow segment 711 drops below P-open, the net force on pressure element 703 may be such that it will again close off tube 701 and fluid flow will stop.

In this second embodiment, there may be a segment 701d, which may be on the outflow side and may also be partially compressed by pressure element 703, due to the stiffness and shape of the fluid path element 701. Thus, there may be a small force on pressure element 703 produced by pressure in tube segment 701d. If the area of segment 701d is much less than the area of segment 701b, the effect of this non-ideal situation can be minimized or made insignificant.

FIGS. 8A-8F show three valves which can be used in alternative embodiments of the configurable fluid delivery system. All three valves 450, 470, and 490 have housings 451, 471 and 491 to contain the fluid and other mechanical parts. All have inlets 455, 475 and 495, outlets 456, 476 and 496, moving elements 452, 472, and 492 which interact respectively with sealing surfaces 454, 474 and 494. The moving elements 452, 472 and 492 are acted upon by input pressures 457, 477 and 497, outlet pressures 458, 478 and 498, external pressures 459, 479 and 499, and force actuators 453, 473 and 493 respectively. Because of the differences in geometry, the flow vs. pressure curves for the three valves differ. As mentioned elsewhere, the force actuators may be passive, for example a spring or bladder, manually adjustable, for example a screw compressing a spring, or controllable by the control unit, for example a solenoid, hydraulic, pneumatic, motor driven springe compression, or other force actuator.

In the valve 450, the outlet pressure 458 and the force actuator 453 push the moving element 452 against the seal 454. The moving member will move to the left, allowing fluid to flow when the force from the inlet pressure 457 is greater than the force from the output pressure 458 and the force actuator 459. The graph in FIG. 8B illustrates this. The vertical axis is flow and the horizontal axis is the output pressure 458, both in arbitrary units. For an output pressure 458 of 0, the graph follows line 440, opening at 2 units. For an output pressure 458 of 1 unit, curve 441 represents the behavior of the valve. It opens at 3 units. Similarly with an output pressure 458 of 2 units, curve 442 indicates that the valve will open at a pressure of 4 units. Note that there can never be flow from the outlet to the inlet, outside of the failure of some part of the system or a negative force on the force actuator 453.

In the valve 470 shown in FIG. 8C, the moving member is slidably sealed at the inlet at 474 and is also slid ably sealed to the housing 474'. This is similar to the valve in FIGS. 6A-6B. The operation of this valve is illustrated in FIG. 8D. Because of the geometry involved, the outlet pressure 478 has little or no effect on the movement of the moving element 472. Thus when the force from the input pressure 477 exceeds the force from the force actuator 473 and the external pressure 479, it will move and fluid can flow. Note that fluid can flow both directions, either from the inlet 475 to the outlet 476 if the inlet pressure 477 is greater than the outlet pressure 478, or from the outlet 476 to the inlet 475 if the outlet pressure 478 is greater than the inlet pressure 477, provided that the inlet pressure 477 is high enough to hold the moving element 472 open. This is the behavior of the high crack pressure valve that is used in a number of the embodiments of this invention.

Figure 8E:
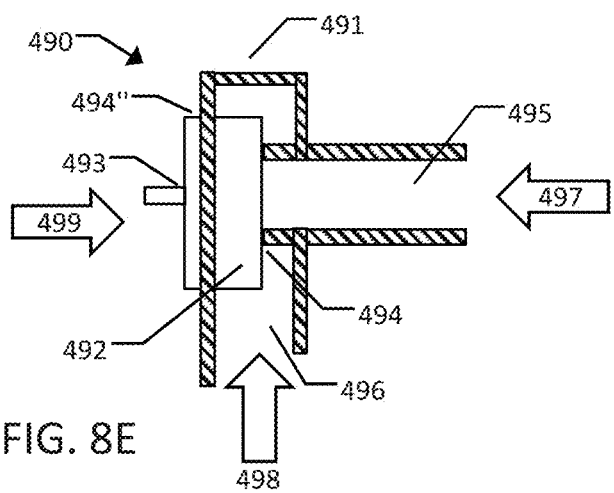
Figure 8F:
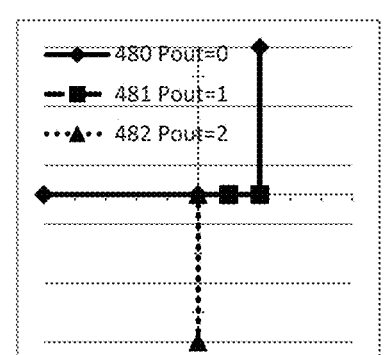

FIG. 8E illustrates a third general type of valve in which the inlet pressure 497 and the outlet pressure 498 both act to push the moving element 492 open against the restraining forces form force actuator 493 and the external pressure 499. FIG. 8F shows the performance curve of this valve. For simplicity in this example, the force from the input pressure 497 and the output pressure 498 are the same per unit pressure. With an output pressure 498 of 0, the valve acts as a normal check valve as show in curve 480, similar to valve 450 with a crack pressure of 2 units. With an output pressure of 2 units, the valve will open as soon as the input pressure 497 goes above zero and fluid will flow from the outlet 495 to the inlet 496, since that is the direction of the pressure differential. The dot or graph 481 represents the situation where the input pressure 497 equals the output pressure 498 and together they are just enough to open the valve but there is now flow because the pressures are equal. If either of the pressures increases a little more, fluid would flow from the high pressure side to the low pressure side.

FIGS. 9A-9D, 10A-10D and 11A-11D illustrate example operation of the example embodiments of the system of this invention with exemplary fluid path arrangements. FIGS. 9A-9D represent example operation of the fluid delivery unit and disposable set presented in FIG. 3D for delivering two or more fluids. In this example, the valves 396 and 398 are absent and instead simple tubes 396' and 398' that conduct the fluid unobstructed or unchanged are shown. Similarly, the selection valve 393 is absent and a simple Y or T 393' combines the two inlets to one outlet 390. FIG. 9A is a graph over time, in arbitrary units, of two fluids being delivered from the system and disposable set of FIG. 3D. FIG. 9B shows the fluid delivery unit 310d, for example, made up of two syringes, the first syringe 801 on the right containing a fluid 1 and the second syringe 802 on the left containing fluid 2. The two syringes may be manually operated or interfaced with two drive units and one or more control units which are not shown. Referring to the graph of FIG. 9A, when the plunger of the first syringe 801 is driven forward, line 851, starting at t=1, the pressure 853 builds up gradually because of the capacitance of the various system components. This drives fluid flow 852 out of syringe 801. Even though or because the motion of plunger 854 of syringe 802 is zero, some of that fluid from syringe 801 flows 855 into syringe 802 to build up pressure 856 in syringe 802 causing a negative flow 855 from syringe 802. This is shown diagrammatically in FIG. 9B where arrow 811 represents the fluid flowing out of syringe 801, arrow 813 represents the fluid flow out the outlet 390 to the recipient, and arrow 812 represents fluid flowing form syringe 801 into syringe 802. Referring back to FIG. 9A, once a steady state is reached at t-2, the pressures 852 and 856 are the same and no more fluid flows 855 into or out of syringe 802 while fluid continues to flow 852 from syringe 801 to the outlet. When plunger motion 851 of syringe 801 stops at t=4, the pressure 853/856 of both syringes 801/802 decreases gradually and there is flow 852/855 or dribble out of both syringes 801/802 even though neither syringe is being driven forward primarily due to the energy stored in the capacitance of the syringes. This is shown diagrammatically in FIG. 9D in which arrow 831 indicates fluid flowing from syringe 801, arrow 832 represents the fluid flowing from syringe 802 and arrow 833 represents a mixture flowing from the confluence at selection valve 392 which reaches the recipient depending generally on the volume of the capacitance of fluid path elements upstream from the confluence and the fluid path volume downstream from the confluence. The ratios of the flows and volumes from the first syringe 801 and the second syringe 802 depend upon among other things the capacitance of the syringes, valves and relevant fluid path elements.

Referring to FIG. 9A, at time t=5, the plunger 854 of syringe 802 begins to move. A similar behavior ensues to that described above, but with syringe 802 replacing syringe 801 and vice versa, where some of the fluid from syringe 802 moves into syringe 801 as it is pressurized, then a steady state is reached at t=6 and then there is dribble from both syringes from t=7 to 8 as the pressure in both syringes returns to 0.

At time t=9, a sequential injection begins with fluid being delivered from syringe 801. The system actions and performance from t=9 to 12 are the same as the actions performance from t=1 to 4. At t=12, the plunger 851 of syringe 801 stops forward motion and the plunger 854 of syringe 802 beings forward motion. Because both syringes are pressurized, ignoring inertia and other second order effects, the fluid flow 852 of syringe 801 stops and the fluid flow 855 of syringe 802 begins. This is represented in the diagram of FIG. 9C, provided the plunger of syringe 801 is not pushed or moved backwards, there is little or no flow from syringe 802, arrow 822 into syringe 801, arrow 821 with no head or motion. The flow of fluid 2 exits through the outlet 390, as illustrated by arrow 823. At t=16 where both syringes stop their forward motion, the flow is similar to that of t=4 to 5 and t=7 to 8 where there is dribble from both syringes to the outlet, as is illustrated in FIG. 9D and described above. Thus, the simplest disposable set has significant drawbacks due to fluid mixing and dribble after the injection. It should be noted that in FIGS. 10A-10D, 11A-11D and 12A-12D, the heavy crosshatch, for example in items 801, 811, and 813, represent the flow of the fluid from first syringe 801. The clear fill, for example in items 802, 822, and 823, represent the flow of fluid from second syringe 802, and the lightly cross hatched items, for example 833, represents the flow that is a mixture of the fluids from syringes 801 and 802. This is simplified to make it more easily communicable by not accounting for the spreading or mixing that can be caused at the interface of successive flows by normal laminar or turbulent flow behavior. One skilled in the art can account for this if needed.

Note that in FIGS. 9A-9D, 10A-10D and 11A-11D, the first injection, from t=1 to 4 can represent the priming of the various fluid path elements, in which case the steady state delivery can be significantly shortened or it can represent the delivery of just fluid 1 to a recipient in a procedure. Similarly, the system actions from t=5 to 8 can represent the fluid priming of the fluid path related to fluid 2 and/or the delivery of fluid 2 alone to a recipient in a procedures. t=9 to 17 represents a two phase injection of fluid 1 followed by fluid 2.

In some procedures, this behavior or performance is not a problem, for example when a syringe full of 100 ml of contrast is delivered to a patient followed by a syringe full of 50 ml of saline. The dribble afterwards is not significant because both syringes are fully dispensed, and the little bit of contrast that gets into the saline does not matter because it is insignificant compared to the total amount given to the patient. In another situation, where multiple mice are sequentially delivered volumes on the order of 50 microliters from a 3 ml syringes with a radiopharmaceutical and saline, this effect leads to significant inaccuracies.

FIGS. 10A-10D illustrate an alternate embodiment utilizing simple one-way check valves for valves 396 and 398. These are the valves, generally with a low crack pressure and where the opening pressure is equal to the crack pressure plus the outlet pressure, as discussed in relation to FIG. 8A. The performance of such an embodiment is illustrated in FIG. 10A. At time t=1, the plunger movement 951 of syringe 801 starts. This pressurizes 953 syringe 801 and fluid flows 952 to the output. Note that there is no flow 955 into or out of syringe 802. This flow pattern is illustrated in FIG. 10B. Valve 398 prevents flow into second syringe 802, arrow 912, when there is flow out of first syringe 801, arrow 911, which flows out to the recipient, arrow 913. From t=5 to 7, the situation is in steady state and fluid 1 is delivered 952. At t=7, the plunger of syringe 801 stops moving 951 and there is a dribble of flow as the pressure 953 in syringe 801 is released. There is no dribble 955 from syringe 802 because there was no pressurization 956 of syringe 802. At t=5, the plunger of syringe 802 begins to move 954, pressure builds up 956, and fluid flows 955. The behavior is now similar to that from t=1 to 5 with second syringe 802 replacing first syringe 801. This is illustrated in FIG. 10C. At t=9, a sequential injection begins, t=9 to 10 is the same as t=1 to 2, as the plunger moves 951, pressure builds up 953 and fluid flows 952 from syringe 801, reaching a stead state delivery from t=10 to 12. At t=12, the plunger of syringe 801 stops moving 951 and the plunger of syringe 802 starts moving 954. Because syringe 802 was not pressurized 956, it takes some time for the pressure 956 and flow 955 to build up. During that transition period, the pressure 953 in syringe 801 will decrease as fluid continues to flow 952 from syringe 801. The flow 952 from syringe 801 will decrease similarly. When the pressure 956 in syringe 802 is greater than the pressure 953 in syringe 801. which has been driving the pressure at the confluence, check valve 396 will close and check valve 398 will open. The fluid flow 955 from second syringe 802 will start and the fluid flow 952 from syringe 801 will stop, and the pressure 953 in syringe 801 will stop decreasing and remain at some level below the pressure 956 in syringe 802. Fluid will flow 955 only from syringe 802. Notice that there has been a small dip or drop in the fluid flow during this transition. Once the flow 955 of syringe 802 has reached its maximum, the flow will continue at that level. At t=16, when the plunger motion 954 of syringe 802 stops, there is residual pressure 956/953 in both second syringe 802 and first syringe 801, respectively. So fluid will flow or dribble 955/952 from syringe 802 and from syringe 801, respectively, and mixture will move into and possibly out of outlet 390. This is illustrated by the arrows in FIG. 10D, with the light crosshatch in arrow 933 representing the mixture.

This embodiment eliminates the problem of one fluid being injected into the fluid path or reservoir of the second fluid during the initial injection, but it does little or nothing to reduce the dribble at the end of the injection. This behavior occurs even for check valves with crack pressures that are more than a few psi, provided that the crack pressure is below the ultimate operating pressure immediately downstream of the valve. In this case, there will be less, but will always be some, dribble or flow after stopping due to the capacitance of the syringe and other fluid path elements upstream of the valves as the pressure in the syringes relieves from the operating pressure to the crack pressure of the valves 396 and 398.

FIGS. 11A-11D illustrate an example embodiment with high crack pressure valves, for example those of FIGS. 6A-6B and FIG. 7, as valves 396 and 398. Considering FIG. 11A, at t=1, plunger motion 991 of first syringe 801 starts. Pressure 993 within syringe 801 builds, expanding the syringe and associated disposables until it reaches the crack pressure of the valve 396, at which time the pressure stops increasing and the flow 992 of syringe 801 begins and quickly goes to the level dictated by the plunger velocity 991. FIG. 11B shows the flow pattern from t=1 to 4. At time t=4, when the syringe plunger velocity 991 stops, the pressure 993 in syringe 801 drops a small amount (not visible on this graph) and the high crack pressure valve closes. Pressure 993 of syringe 801 stays at the valve crack pressure, provided the syringe piston is not moved back or pushed back by the pressure 993 in syringe 801. FIG. 11D illustrates the flow pattern at this point; there is no flow. At time t=5, syringe 802 goes through a similar behavior: the plunger of first syringe 802 moves 994, pressurizing 996 the second syringe 802, and when the crack pressure of the valve is reached, the pressure stops increasing and there is flow 995 from second syringe 802. FIG. 11C illustrates the flow at this point. When the plunger of syringe 802 stops moving, the pressure quickly drops and holds at the crack pressure of the valve and the flow stops. FIG. 11D illustrates the flow pattern at this point; there is no flow or dribble. Note that some of fluid displaced by the plunger motion remains trapped in the syringe and associated disposables due to their expansion with pressure that is due to their capacitance. This represents an inaccuracy in the fluid volume delivery, for example the plunger moved enough to dispense 4 ml under no back pressure conditions, but only 3 ml were dispensed and 1 ml was used to pressurize the fluid path elements. In the embodiments described in relation to FIGS. 9A-9D and 10A-10D, because the ending pressure was close to 0, all the volume displaced by the plunger was delivered to the recipient, but the flow rate (delivery over time) was not ideal, illustrated in the slow rise in velocity and the slow fall or dribble after the plunger stopped moving. This volume inaccuracy on the first fluid delivery is insignificant if the first delivery is used to prime the system. It can be thought of as priming the capacitance volume of the system.

Further considering FIG. 11A, at t=9, plunger motion 991 of first syringe 801 begins again. Because the system remained pressurized at the crack pressure of the valve, the majority of the capacitance is still filled, and so a very small forward motion 991 increases the pressure 993 enough to open the valve and start the fluid flow 992. At t=12, the plunger motion 991 of syringe 801 stops and the flow 992 also stops quickly. At the same time, the plunger of syringe 802 starts moving 994 forward. This almost instantly increases the pressure 996 in syringe 802 to the point that fluid flows 996 from syringe 802. At t=16, the plunger velocity 994 of syringe 802 drops to 0 and motion stops. The flow 995 of syringe 802 also stops very quickly. Note that, in this embodiment, once the fluid delivery unit is pressurized to the valve's crack pressure, any displacement of the syringe plunger or actuator displaces fluid which is delivered downstream. This performance is as close to the ideal independent fluid delivery as this system can achieve, with rise and fall times limited by only by actuator performance and the non-ideality in the valve flow vs. pressure graph as discussed elsewhere.

Note that, in FIGS. 11A-11D, there is preferably some means or mechanism to permit the pressure to be relieved behind valves 396 and 398. Examples of such may include: having the syringe plunger reverse sufficiently, either passively or actively; having separate relief valves; or incorporating a lever or adjustment into the valves 396 and 398 themselves, for example having a lever to relieve the spring force on element 613 or pull on rod 614 to open the valve, either manually or through system control. A further example may include an additional valve that can relieve the pressure to a waste bag or to the source of the fluid through the fluid path elements (not shown) used to fill same.

In the embodiments discussed with respect to FIGS. 9A-9D, 10A-10D and 11A-11D, the system behavior, that is the action of the actuator or delivery units under the control of control unit 130, is to move the actuator (a plunger in this example) from one position to a new position and then hold the actuator at that new position. This can be accomplished through a controllable or controlled mechanical means, such as an optionally releasable ratchet or through an active servo under the control of control unit 130. This strategy of holding the piston in position is necessary in the situation of FIG. 9A because pressurizing one syringe pressurizes any other syringes that are connected to it, and if their plungers were not held in position, the pressure would push them backwards. In the case where the system is operated manually, this is very difficult to do. In that case, ratchets may be used to prevent backward motion or there may be a stopcock placed at selector valve 393, which may be manually activated by the user.

Alternative embodiments of this invention may employ one or more of a combination of various system control or actuator strategies with one or more of a combination of valve and fluid path element configurations. At any point in time, there may be no actuator or one or more actuator that is/are activated by the control unit 130. When activated, the actuator may be moving forward, holding a position, or moving in reverse, for example to fill or relieve pressure. When not activated, the actuator may hold position due to a built-in, optionally selectable, breaking mechanism or due to friction inherent in the actuator or fluid delivery unit. One actuator strategy at the end of the delivery of a fluid is for the actuator to float or move based upon pressure inside the fluid delivery unit. There commonly, but not necessarily, is a friction associated with the fluid delivery unit or the actuator, for example sliding a syringe plunger or compressing a tube in a peristaltic pump. As a result, there may be a static and dynamic frictional force to be overcome before movement happens. A second strategy at the end of a delivery of a fluid is to move and hold position as discussed above, either with mechanical means such as ratchets or under active control from control unit 130. Another alternate strategy is to move the actuator to deliver fluid, and when the actuator gets to its final position, to release the actuator and let any pressure in the fluid delivery unit (a syringe in this example) drive the actuator back to reduce the pressure in the system. For example, this can be used with check valves to reduce dribble after the delivery. It can also be used with high crack pressure valves to reduce the pressure in the system and reduce the energy that the system uses. Another alternative strategy is, after delivery by an actuator, to actively control the actuator to a position which causes a specific pressure to be developed in the fluid delivery unit.

One example is to pull the actuator back until the pressure in the fluid delivery unit is zero. A second example is to pull the fluid actuator back so that there is a negative pressure in the fluid delivery unit to fill the fluid delivery unit from an external reservoir.

In an embodiment in which the actuator moves back, either under active system position control or passively under the influence of pressure retained in the fluid delivery unit, the actuator may measure the volume displacement so that it can use this information to compensate when the next fluid delivery is to take place. For example, if the actuator moves backward the equivalent of 2 ml, then if the next injection calls for an injection of 10 ml, the system control unit would, for example, direct the actuator to move or deliver 12 ml, recognizing that it will likely take the first 2 ml of motion or apparently delivery to pressurize the system so that delivery out of the system can start to occur.

The operation of one alternative embodiment utilizing backward motion of one or more actuators to improve system performance is shown in FIGS. 12A-12D. This embodiment is essentially the same physical embodiment discussed elsewhere and is shown in FIGS. 10A-10D, which has the valves 396 and 398 being simple check valves. At t=1, the behavior is the same, the plunger of first syringe 801 moves 951' forward, pressurizing 953' syringe 801 and causing fluid to flow 952'. The difference occurs at the end of the injection, t=4. At this point, the velocity 951' of the plunger of syringe 801 goes negative for a short time, quickly dropping the pressure 951' in syringe 801 which quickly reduces the flow 952' from syringe 801. Thus there is little or no dribble. The reverse movement can be passive, meaning that the plunger is pushed back by the pressure of the fluid in the syringe itself. Alternatively, the plunger can be moved back actively by the relevant control unit. As mentioned elsewhere, it is advantageous for the control unit to remember the amount of reverse motion that happened, and optionally the pressure that had been developed, so that it can use such information in the control algorithm and strategy going forward so as to increase the accuracy of future volumes delivered and the sharpness of future flow profiles.

At t=5, the second syringe 802 is activated and the behavior is similar. The reverse motion 956' for syringe 802 at t=7 reduces or practically eliminates the dribble. At t=9, a two phase injection begins. The operation through t=13 is the same. Sometime after the steady state is reached but before the end of the injection, the pressure 953' in syringe 801 is reduced to zero by moving 951' the plunger of syringe 801 backward an appropriate amount, either actively or passively. This means that there will be no dribble from syringe 801 at the end of the injection. At t=16, the behavior of the system is the same as at t=7, the plunger of syringe 802 moves 954' quickly backward to drop the pressure 956' in syringe 802 which quickly stops the flow 955' from syringe 802.

In an alternative embodiment, the valves 396 and 398 may be different valves and the operating strategies of the actuators may be different. For example, if fluid 1 is a radioactive fluid or gene therapy whose precise delivery of small volumes is critical, valve 396 may be a high crack pressure valve. If fluid 2 is saline that is being used to simply prime the system to remove air and to flush the line 390 of fluid 1, then dribble, volume precision, and a rapid rise may not be important for fluid 2 and so valve 398 may be a simple check valve and the actuator operation can be a move and hold position approach. Optionally, syringe 802 may have no valve in its path to the confluence, that is valve 398 is absent.

Various system designs and strategies to achieve controlled fluid delivery without valves are discussed in U.S. patent application Ser. No. 13/799,426 referenced above.

It will be recognized by those skilled in the art that the capacitance of a system and fluid path elements is not necessarily constant, and may change with time, temperature and pressure. If the capacitance reduces with pressure, for example with a syringe in a pressure jacket, the high crack pressure valve may not need to have a crack pressure higher than the normal operating pressure of the system, but only high enough to take up the majority of the capacitance as the syringe moves or swells to fill the pressure jacket. Similarly, other aspects of the fluid system and fluid path elements can affect the relationship of the high crack pressure valve to the normal operation pressure.

Figure 13A:
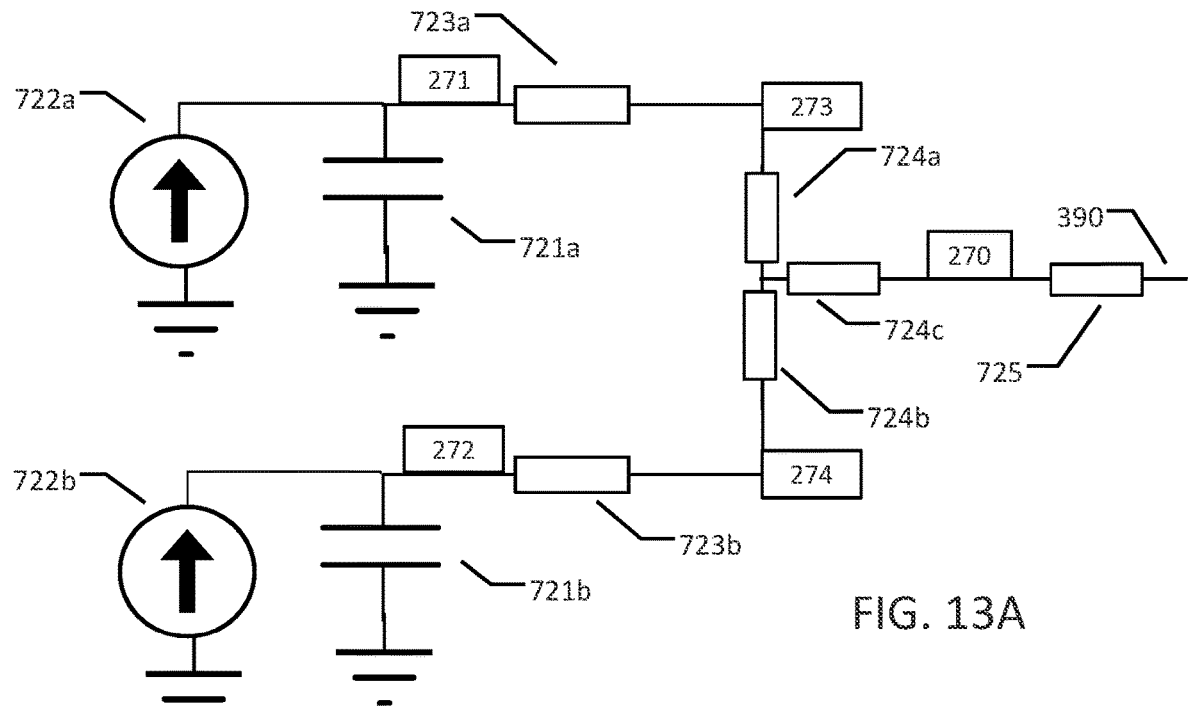
FIGS. 13A-13B illustrate models that can be used by a control unit in control of the configurable fluid delivery system.

In an embodiment, to improve the accuracy, performance and/or safety of fluid delivery, the control unit may employ a system model as shown in FIG. 13A that includes models of the non-idealities of syringe capacitance and fluid path resistances. This model represents the system of FIGS. 9A-9D in which there are no valves. In the electrical analog of a fluid flow system, charge corresponds to voltage, current to flow, fluid path resistance to electrical resistance, inertia to inductance, and pressure to voltage. The motion of the pistons is modeled as current sources 722a and 722b driving current (fluid) into the syringe. The syringe capacitances are modeled by capacitors 721a and 721b. As shown in FIG. 32 of International Patent Application No. PCT/US2014/026324 to Schriver et al., incorporated herein by reference, the value of the capacitance depends upon the piston position, so they are not simple, fixed capacitors. The capacitance has a number of potential contributors, for example movement of the syringe against its mounting, stretching of the syringe inside a pressure jacket if any, compression of any elastomeric components or seals, and compression of any air bubbles that may be left in the fluid. Some of these are non-linear, for example the syringe has a relative high capacitance as it expands, but once it engages with the pressure jacket, the capacitance decreases considerably due to the pressure jacket stiffness. The output of the syringes flows through resistors 723a and 723b respectively, which model the resistance of the fluid paths to the junction, confluence, or flow mixing device. The resistance depends upon the geometry of the fluid path elements, e.g., ID, length, bends, etc. and the viscosity of the fluid, which itself depends upon the temperature and any mixing which has occurred, and if the fluid is non-Newtonian, on the fluid velocity itself. The resistance of the mixing device is illustrated as 3 resistors in a T, 724a, 724b, and 724c. This separation is done to simplify the modeling because the resistance of 724a depends upon the viscosity (and temperature) of the fluid in that syringe; the resistance 724b depends upon the viscosity (and temperature) of the fluid in its respective syringe; and the resistance 724c depends upon the viscosity of the resulting mixture, which depends upon the two flows coming into the mixing chamber. The resistance 725 represents the resistance of the remainder of the downstream fluid path elements and has a mixture of fluids in it. The behavior of this model can be simulated with readily available simulation tools like SPICE all the way up to more sophisticated models such as Matlab/Simulink or COMSOL. System models such as this can even handle the fact that the fluid path element resistance depends upon the viscosity, and the syringe capacitances depend upon the volume remaining. These types of models can be implemented in the control unit or in a separate computational device. These types of models can be used by the user or the control unit during assembly of a system to inform the user of the system capabilities and/or during system operation to determine optimum actuator or system operation actions to deliver the desired fluid delivery profile and/or to determine if the delivery is able to be continued safely and effectively.

In alternative embodiments, the fluid control module can employ a more sophisticated model. For example, the inertia of the motor can be modeled as an inductance between the current source and the capacitor. Similarly, fluid flow inertia in the fluid path elements can be modeled as inductances in line with the fluid path resistances, and the fluid path capacitances can be modeled as capacitors to ground. A more sophisticated embodiment that can be employed, if useful, is to use distributed lump parameters or transmission line models for the fluid path elements. Additional control algorithms are described in International Patent Application No. PCT/US2014/026324 above.

Figure 13B:
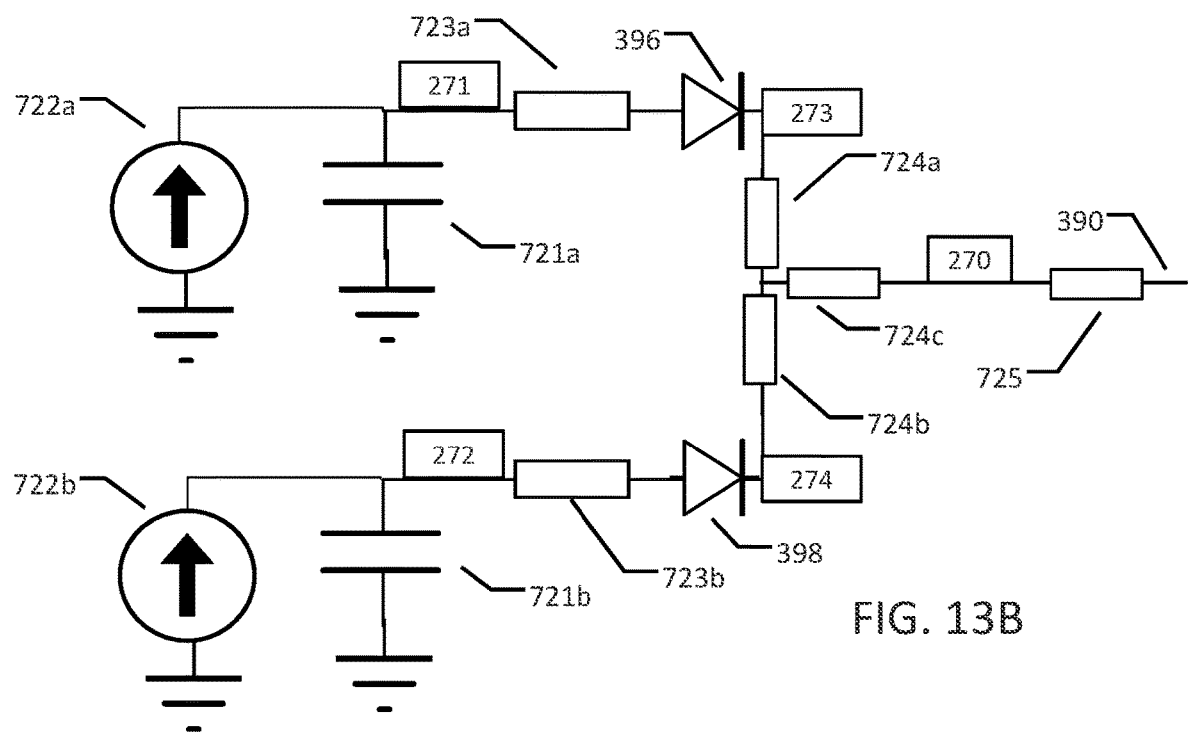

FIG. 13B represents a model which can be included in an embodiment of the control unit to model operation with one or more valves in one or more fluid lines. For example, in the system with valves 398 and 398 being low crack pressure check valves, whose performance is discussed with respect to FIGS. 10A-10D, the model element is a diode with an I-V or flow-pressure relationship as shown in FIG. 8B. The modeling in the control unit can be used to predict and assess the performance of the system.

For example, in an embodiment described and operated as discussed in relation to FIGS. 12A-12D, if the pull back of the piston is active, that is under servo control, the control unit can estimate the amount of capacitance volume in the system from general system design properties or via experimentally or experientially determined performance data, for example that given in FIG. 32 of International Patent Application No. PCT/US2014/026324 above. In the case where the syringe is full and the pressure reached is 200 psi, then the injector would expect a capacitance volume of about 4 ml. If the pressure reaches 1200 psi for a nearly full syringe, the expected capacitance volume is 10 ml. For a nearly empty syringe, the capacitance volumes are 2 ml for 200 psi and 7 ml for 1200 psi. Pulling back a volume equal to the expected capacitance will significantly reduce the dribble. In addition, before pulling back, the injector can add the amount of the expected capacitance to the volume to be delivered, for example if the user has selected a volume of 30 ml to be delivered, the total volume the injector piston moves would be 34 ml (30+4) if the syringe is nearly full and the pressure at the end of the injection reaches 200 psi. Upon reaching 34 ml of displaced volume, the piston would stop and move backwards, more rapidly stopping the dribble at the end of the injection. If the injection pressure would reach the 1200 psi point with the syringe nearly full, the injector would continue delivering fluid until the piston had moved 40 ml (30+10) before stopping and moving backwards. Similarly, if the syringe is nearly empty, the volumes of piston travel would be 32 ml (30+2) and 35 ml (30+5) at 200 psi and 1200 psi, respectively. One benefit of selected embodiments of a configurable system of this invention is that in some embodiments the control unit can incorporate multiple, general or generic algorithms for compensating for the non-idealities, non-linearities or limitations of various fluid delivery units or actuators. With information from the data storage device associated with various components or data from the user or user selectable menus, the user and/or the system can select the most appropriate algorithm or approach, even to the point of suggesting fluid path elements such as check valves, for the user to include when configuring the system, and once the system is configured, operating the system with the algorithm that best meets the user's delivery needs. For example, when delivering full or almost full syringes, syringe capacitance is not much of an issue, and a simple push and stop algorithm is appropriate. Alternatively, when the system recognizes that the user desires to or is trying to deliver relatively small volumes from larger syringes, the system can recommend the inclusion of check valves and the implementation of the improved algorithms, for example one or more of those described herein.

To accommodate the delivery of multiple fluids and different system capabilities, multiple high crack pressure valves can be used in series, for example before various confluences or after items with significant capacitances, provided that the downstream valves had lower crack pressures than the upstream valves. As explained herein, this valve serves to isolate the capacitance volumes of the fluid path elements, the fluid delivery units, and/or the fluid actuator units.

With the explanations and disclosures made herein, one skilled in the art can recognize that there are a number of possible dimensions of integration. The implementation of a configurable fluid delivery system requires an approach to each of these that involves a specific choice or implementation, e.g., requiring every aspect to operate to a pressure limit of at least 300 psi, or to define specific interface aspects, or not to specify one or more aspects and let the user handle or figure it out.

Various embodiments of this configurable fluid delivery system can employ various levels of integration along various dimensions of interaction. A useful configurable system can be made of units that only share data communications with each other. This data communication can occur before injection, during injection, during injection with real time control and interaction, and/or after an injection. A further dimension of integration involves programming, for example, setting up an injection sequence. Each unit can have an interface of some type and be programmed independently, or all programming may be done on a single central user interface, or any combination in between, including having both independent and central programming capability, with a change on any one interface being rapidly displayed on the other(s). A further dimension of integration is coordination of operation. This coordination can take place through a central control unit, individual control units which communicate with each other, or a combination of both. As mentioned elsewhere, a hierarchical approach is preferred with some local control to allow customizability to the need and capability of each unit and some central oversight to facilitate ease of programming coordination for accuracy and safety. The optional communications with one or more sensors assessing the patient is another dimension. Such communications can go to the central control unit or to a specific fluid delivery unit or fluid actuator unit. Similarly, operation or action based upon that data can be done in the central control unit or in functionality at a lower level. There are almost innumerable communication architectures, methods, mediums and protocols known to those skilled in the art, ranging from peer-to-peer to master-slave topologies which can be suitable to this configurable fluid delivery system.

An additional dimension of interaction is physical. For example, the units can be separate and be set on a bench by the user, rack mounted, mounted onto a plate as mentioned elsewhere, or preassembled into a single unit with multiple fluid capabilities. Power is another dimension of integration. Each unit may have its own AC power plug or adapter. Alternatively, conditioned power can be supplied via some type of bus, similar to what is done in a desktop personal computer. For safety, in selected embodiments, individual units may be powered through a power bus or panel, either DC or AC, which allows the control unit to cut power to one or more fluid delivery units or fluid actuator units to instantly stop a fluid delivery if something unsafe is detected. Alternatively, one or more units may be powered by battery or other energy storage means, for example by gravity, spring, vacuum or compressed gas. Fluid path is another dimension of integration. The standard luer connections can be utilized. Alternatively, if small volumes or cells will be delivered, connectors that minimize dead volumes or turbulence and shear may be used.

Ultimately, some or all of the fluid delivery units and/or fluid actuator units may come fully pre integrated along one or more dimensions and be considered as a single unit for further integration along other dimensions.

To better enable someone skilled in the art to implement this invention, the following list of example dimensions of integration is provided: unit packaging and housings, mounting and support, power, fluid path elements, fluid sources, communications, protocol or program data, relevant data storage, unit and system state machines and real time control, safety checks, patient, unit, and system sensors, actual and/or achieved data, business and usage related data, operator and patient identification data, and regulatory approvals. Optional additional aspects and dimensions of integration for a fluid delivery unit being used with a larger system, for example, an imaging system, have been disclosed and discussed in U.S. Patent Application Publication 2009/0177050 to Griffiths et al., which is incorporated herein by reference. Once one skilled in the art has this list in mind, they will be able to develop a variety of implementation approaches which provide sufficient configurability and integration for their specific use.

With the explanations and disclosures made herein, one skilled in the art can recognize the behavior of the system for more complicated injection procedures, for example including multiple phases and/or phases involving the simultaneous delivery of 2 or more fluids with a controlled ratio of delivery. One skilled in the art can also recognize that the various fluid path elements, especially the valves, do not need to be identical for the system to work satisfactorily for a particular procedure or need. In an example procedure, it may only matter that there be no dribble of fluid from syringe 801. Pushing of fluid from first syringe 801 into the line of second syringe 802 may not matter because the fluid is subsequently delivered to the recipient during the second or flush phase. In this case, a high crack pressure valve need only be provided for syringe 801, valve 396 and valve 398 can each be a normal low crack pressure check valve or a fluid path element of sufficient volume such that fluid going into the fluid path elements connecting to syringe 802 are sufficiently flushed during the delivery of the fluid from syringe 802. Thus, each of the fluid delivery units 260a-260d may have different valves or no valve (the valve is a simple tube) associated with their output as the need, application, or procedure requires.

In another non-limiting example, an inline high crack pressure valve may be used with a fluid actuator and/or fluid delivery unit which is a pulsatile pump such as a diaphragm or peristaltic pump. Accumulators, for example, a spring or pressure biased reservoir, can be placed on the output of such pumps to attempt to smooth the flow, but accumulators may operate effectively only within a limited pressure range. By placing a high crack pressure valve downstream of the accumulator, the accumulator may consistently operate at a pressure in the same range as the high crack pressure valve, independent of the downstream pressure fluctuations. As a result, potential oscillations in fluid flow due to the operation of the pump may be damped. The respective pressure ranges of the accumulator and the high crack pressure valve, in addition to the accumulator volume, may depend or be chosen to depend upon at least in part on the operating pressure of the pump, the specifics of the fluid path, the fluid volumes and flow rates for delivery, and the pump output pulsatility. Additionally, an inline high crack pressure valve may be as useful with single fluid delivery devices as with multiple fluid delivery devices.

In some situations, such as CT contrast delivery, the pressure developed by the pumps during normal injections can approach or exceed 300 psi. In such cases, an opening or crack pressure may be about 350 psi or more. In angiography, an opening or crack pressure may be over 1000 psi. In alternative procedures, such as a fluid injection into a mouse, the injected volume may be small, on the order of 50 microliters, and the injection pressures involved may be on the order of 10's of psi. Therefore, for procedures using small animals, a crack pressure of 50 psi or even 20 psi may be sufficient. In one non-limiting example, each application may have associated with it a specific high crack pressure valve having a set and procedure specific P-open. In an alternative non-limiting example, a single high crack pressure valve having an adjustable P-open pressure may be used among a variety of procedures. One embodiment of an adjustable high crack pressure valve may include a user-adjustable screw to compress a spring, optionally with a dial or indicator so that the operator can assess the compression and determine that it is correct. Alternatively, the system may include a sensor through which the control unit can assess the correct compression, preparation or operation of the high crack pressure valve. This can improve efficiency because the system only needs to develop the pressure that is sufficient to deliver the fluids and ensure tight boluses or sharp fluid flow and prevent mixing and dribble, whereas with a non-adjustable valve, the valve crack pressure is preferably set for the highest pressure that the system needs or can accommodate. In another embodiment of an adjustable high crack pressure valve, an adjustable electromechanical actuator may be used to apply the variable clamping force. Such automated adjustable high crack pressure valves may be useful for real time modification by the system controller. In one non-limiting example, the control unit may alter the variable clamping force based at least in part upon data received by the control unit from one or more pressure sensors in the system.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated in this disclosure, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is also to be understood that the terminology used in this disclosure is for the purpose of describing particular embodiments only, and is not intended to be limiting.

With respect to the use of substantially any plural and/or singular terms in this disclosure, those having skill in the art can translate from the plural to the singular and/or from the singular to the plural as is appropriate to the context and/or application. The various singular/plural permutations may be expressly set forth in this disclosure for sake of clarity.

It will be understood by those within the art that, in general, terms used in this disclosure, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be understood that terms such as sliding may include movement, rotation, deflection, or other relative positional changes.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

From the foregoing, it will be appreciated that various embodiments of the present disclosure have been described for purposes of illustration, and that various modifications may be made without departing from the scope and spirit of the present disclosure. Accordingly, the various embodiments disclosed are not intended to be limiting, with the true scope and spirit being indicated by the following claims.

What is claimed is:

1. A fluid delivery system for controlled delivery of a fluid to a recipient, the fluid delivery system comprising:
a fluid delivery unit for pressurizing and enabling delivery of the fluid to the recipient, the fluid being acquired from a source of the fluid via a source outlet;
a high crack pressure valve having an inlet, an outlet and a moveable element directly acted upon by fluid pressure in the inlet and the outlet, the inlet being adapted to receive the fluid pressurized by the fluid delivery unit and the moveable element being adapted to transmit to the outlet the fluid received from the inlet when the fluid at the inlet reaches a pressure at least equal to a crack pressure threshold of the high crack pressure valve; and a fluid path element for receiving the fluid from the outlet of the high crack pressure valve and conveying the fluid to any remaining system components for delivery to the recipient, wherein the fluid pressure in the outlet of the high crack pressure valve has little or no effect on movement of the moveable element, and wherein the movable element is further acted upon by restraining forces from an external pressure and a force actuator which restrain movement of the movable element in response to fluid pressure at the inlet.

2. The fluid delivery system of claim 1, further comprising a control unit to control delivery of the fluid wherein the control unit controls at least one of the fluid delivery unit and the high crack pressure valve.

3. The fluid delivery system of claim 2, wherein the control unit controls the movable element of the high crack pressure valve.

4. The fluid delivery system of claim 1, wherein the high crack pressure valve is a spool type high pressure crack valve and the force actuator is selected from a spring and a pressurized bladder.

5. A high crack pressure valve comprising:
an inlet adapted to receive a medical fluid pressurized by a pump;
an outlet in fluid communication with a fluid path element, wherein the fluid path element is in fluid communication with downstream system components of a fluid delivery system; and
a moveable element directly acted upon by fluid pressure in the inlet and the outlet, the movable element having a crack pressure threshold, wherein the moveable element has a first closed position and a second open position, wherein the moveable element moves from the first closed position to the second open position when the fluid pressure of the medical fluid at the inlet is greater than or equal to the crack pressure threshold and wherein the inlet is in fluid communication with the outlet when the moveable element is in the second open position, and
wherein the fluid pressure in the outlet of the high crack pressure valve has little or no effect on movement of the moveable element from the first closed position to the second open position, and
wherein the movable element is further acted upon by restraining forces from an external pressure and a force actuator which restrain movement of the movable element in response to fluid pressure at the inlet.

6. The high crack pressure valve of claim 5, wherein the fluid pressure of the medical fluid at the inlet moves the moveable element between the first closed position and the second open position to maintain a pressure within the fluid delivery system at the crack pressure threshold.

7. The high crack pressure valve of claim 5, further comprising at least one sealing surface, and wherein the force actuator is selected from the group consisting of a passive force actuator, a manually adjustable force actuator, and a controllable force actuator.

8. The high crack pressure valve of claim 7, wherein the force actuator is a passive force actuator selected from a spring and a bladder.

9. The high crack pressure valve of claim 7, wherein the force actuator is a manually adjustable force actuator comprising a screw compressing a spring, wherein the screw controls a force of compression of the spring.

10. The high crack pressure valve of claim 7, wherein the force actuator is a controllable force actuator controlled by a controller, wherein the controllable force actuator is a solenoid driven spring compression, a hydraulic driven spring compression, a pneumatic driven spring compression, or a motor driven spring compression.

11. The high crack pressure valve of claim 7, wherein the high crack pressure valve is a spool type high crack pressure valve and wherein the moveable element comprises an internal sliding element adapted to block fluid flow.

12. The high crack pressure valve of claim 11, wherein the force actuator is configured to resist movement of the internal sliding element.

13. A fluid path comprising:
a fluid inlet tubing element;
a fluid outlet tubing element; and
a high crack pressure valve having an inlet in fluid communication with the fluid inlet tubing element, an outlet in fluid communication with the fluid outlet tubing element, and a moveable element directly acted upon by fluid pressure in the inlet and the outlet, the movable element having a crack pressure threshold, wherein the moveable element has a first closed position and a second open position, wherein the moveable element moves from the first closed position to the second open position when the fluid pressure of a medical fluid at the inlet is greater than or equal to the crack pressure threshold, and wherein the inlet is in fluid communication with the outlet when the moveable element is in the second open position,
wherein the fluid pressure in the outlet of the high crack pressure valve has little or no effect on movement of the moveable element from the first closed position to the second open position, and
wherein the movable element is further acted upon by restraining forces from an external pressure and a force actuator which restrain movement of the movable element in response to fluid pressure at the inlet.

14. The fluid path of claim 13, wherein the fluid pressure of the medical fluid at the inlet moves the moveable element between the first closed position and the second open position to maintain a pressure within the fluid path at the crack pressure threshold.

* * * * *

UNITED STATES PATENT AND TRADEMARK OFFICE
CERTIFICATE OF CORRECTION

| | | |
|---|---|---|
| PATENT NO. | : 12,011,568 B2 | Page 1 of 1 |
| APPLICATION NO. | : 17/372673 | |
| DATED | : June 18, 2024 | |
| INVENTOR(S) | : Uber, III et al. | |

It is certified that error appears in the above-identified patent and that said Letters Patent is hereby corrected as shown below:

On the Title Page

Item (56), under "OTHER PUBLICATIONS", in Column 2, Line 1, delete "The" and insert -- A copy of the --, therefor.

In the Specification

In Column 1, Lines 11-12, delete "2014, which" and insert -- 2014, now U.S. Pat. No. 11,058,811, which is a --, therefor.
In Column 3, Line 4, delete "FIG. 8A-8F" and insert -- FIGS. 8A-8F --, therefor.
In Column 6, Line 67, delete "others" and insert -- other --, therefor.
In Column 8, Line 37, delete "uses" and insert -- of uses --, therefor.
In Column 10, Line 21, delete "fluid the delivery unit 110" and insert -- fluid delivery unit 110 --, therefor.
In Column 13, Line 11, delete "previous" and insert -- previously --, therefor.
In Column 13, Line 31, delete "for example." and insert -- for example, --, therefor.
In Column 19, Line 32, delete "segment" and insert -- segments --, therefor.
In Column 20, Line 54, delete "force actuator 459." and insert -- force actuator 453. --, therefor.
In Column 20, Line 66, delete "slid ably" and insert -- slidably --, therefor.

Signed and Sealed this
Twenty-second Day of October, 2024

Katherine Kelly Vidal
*Director of the United States Patent and Trademark Office*